United States Patent [19]
Kolhouse et al.

[11] Patent Number: 5,800,979
[45] Date of Patent: Sep. 1, 1998

[54] GAS CHROMATOGRAPHY/MASS SPECTROMETRIC DETERMINATION OF FOLIC ACID COENZYMES

[76] Inventors: J. Fred Kolhouse, 480 S. York St., Denver, Colo. 80209; John C. Deutsch, 2508 E. 11th Ave. #504, Denver, Colo. 80206; C. R. Santhosh-Kumar, 12457 W. Arkansas Ave., Lakewood, Colo. 80228

[21] Appl. No.: 619,091

[22] Filed: Mar. 20, 1996

Related U.S. Application Data

[63] Continuation of Ser. No. 347,855, Dec. 1, 1994, abandoned.

[51] Int. Cl.[6] ................. C12Q 1/00; C12Q 1/32
[52] U.S. Cl. ......................... 435/4; 435/26
[58] Field of Search ............ 435/4, 26; 514/52; 544/261

[56] References Cited

U.S. PATENT DOCUMENTS

| | | | |
|---|---|---|---|
| 3,989,812 | 11/1976 | Barrett et al. | 424/1 |
| 4,091,087 | 5/1978 | Barrett et al. | 424/1 |
| 4,135,880 | 1/1979 | Mangiardi | 23/230 B |
| 4,247,453 | 1/1981 | Ali | 260/112.5 |
| 4,276,280 | 6/1981 | Akerkar et al. | 424/1 |
| 4,940,658 | 7/1990 | Allen | 435/4 |
| 5,012,052 | 4/1991 | Hayes | 250/288 |
| 5,124,267 | 6/1992 | Humpel et al. | 436/518 |
| 5,212,096 | 5/1993 | Kolhouse | 436/93 |

OTHER PUBLICATIONS

ETO 1, Determination of Three Different Pools . . . Anal Biochem 109 167–184 1980.

Antony, A,C, et al., "Isolation, characterization, and comparison of the solubilized particulate and soluable folate bonding proteins from human milk," *J. Biol. Chem.* (1982) 257:10081–10089.

Babior, B.M., "Metabolic aspects of folic acid and cobalamin," In *Hematology*, (Williams, W.J. et al. Eds.) McGraw Hill, New York, NY (1990) pp. 339–355.

Biermann, C.J. et al., "Analysis of amino acids as tert. –butyldimethylsilyl derivatives by gas chromatography," *J. Chromotography* (1986) 357:330–334.

Blair, J.A. and Saunders, K.J., "A Convenient method for the preparation of dl–5–methyltetrahydrofolic acid (dl–5, 6, 7, 8–tetrahydropteroyl–L–monoglutamic acid)," *Anal. Biochem.* (1970) 34:376.

Botez, M.I. et al., "Neurologic disorders responsive to folic acid therapy," *Can. Med. Assoc. J.* (1976) 115:217–223.

(List continued on next page.)

*Primary Examiner*—Ralph Gitomer
*Attorney, Agent, or Firm*—Greenlee, Winner and Sullivan, P.C.

[57] ABSTRACT

A method for determination of in vivo concentrations in a body fluid of one or more folate co-enzymes is provided including the steps of (a) combining a known amount of at least one folate internal standard with a body fluid collected in vitro, said body fluid containing at least one co-enzyme; (b) at least partially purifying the endogenous and internal standard folates from other components in the in vitro body fluid; (c) quantitating the endogenous folate coenzymes in the purified in vitro body fluid of step (b) by gas chromatography/mass spectrometry analysis; and (d) determining the in vivo concentration of folate coenzymes by correcting the quantitated in vitro endogenous concentrations for endogenous losses as reflected by the losses in the known amounts of the internal standards. Quantitation of total folates or single folate co-enzymes aids in the diagnosis and treatment of a number of clinical conditions involving folate deficiencies including megaloblastic anemia, neurological and psychiatric disorders and vitamin $B_{12}$ deficiency.

6 Claims, 8 Drawing Sheets

OTHER PUBLICATIONS

Bratton, A.C., "A new coupling component for sulfanilamide determination," *J. Biol. Chem.* (1939) 138:537–550.

Brody, T. et al., "Folic acid," In *Handbook of Vitamins*, (Machlin, L.J. Ed.), Marcel Dekker, Inc. New York, NY (1984) pp. 459–496.

Brown, R.D. et al., "Red cell folate assays: some answers to current problems with radioassay variability," *Pathology* (1990) 22:82–87.

CDC (1992) MMWR 41, RR14, 1–7.

Dawson, D.W. et al., "Laboratory diagnosis of megaloblastics anaemia: current methods assessed by external quality assurance trilas," *J. Clin. Pathol.* (1987) 40:393–397.

Deutsch, J.C., Kolhouse, J.F., "Ascorbate and dehydroascorbate measurements in aqueous solutions and plasma determined by gas plasma determined by gas chromatography-–mass spectrometry," *Anal. Chem.* (1993) 65:321–326.34.

Doub, L., Vanderbilt, J.M., "The ultraviolet absorption spectra of simple unsaturated compounds. I. Mono– and ρ–disubstituted benzene derivatives," *J. Am. Chem. Soc.* (1947) 69:2714–2723.

Eicke, A. et al. "Secondary ion mass spectrometry of folic acid analogues," *Anal. Chem.* (1983) 55:178–182.

Eto, I. and Krumdieck, C.L., "Determination of three different pools of reduced one–carbon–substituted folates," *Anal. Biochem.* (1980) 109:167–184.

Fleming, A.F. et al., "Assay of serum and whole blood folate by a modified aseptic addition technique," *Am. J. Clin. Nutr.* (1971) 24:1257–1264.

Gilos, C.R. and Dunbar, D.R., "Measurement of low serum and red cell folate levels: a comparison of analytical methods," *Med. Lab. Sci.* (1987) 44:33–40.

Godfrey, P.S.A. et al., "Enhancement of recovery from psychiatric illness by methyfolate," *Lancet* 336:392–395 (1990).

Gregory, J. F. III, et al., "Relative bioavailability of deuterium–labeled monoglutamyl and hexaglutamyl folates in human subjects," *Am. J. Clin. Nutr.* (1991) 53:736–740.

Gunter, E.W. and Twite, D.B., "Improved materials for long–term quality–control assessment of erythrocyte folate analysis," *Clin. Chem.* (1990) 36:2139.

Hansen, S.I. et al., "Immobilized purified folate–biniding protein: binding characteristics and use for quantifying folate in erythrocytes," *Clin. Chem.* (1987) 33:1360–1363.

Harper, J.M. et al., "Erythrocyte folate levels, oral contraceptive use and abnormal cervical cytology," *Acta Cytol.* (1994) 38:324–330.

Herbert, V. and Zalusky, R., "Interrelations of vitamin $B_{12}$ and folic acid metabolism: folic acid clearance studies," *J. Clin. Invest.* (1962) 41:1263–1276.

Herbert V., "Experimental nutritional folate deficiency in man," *Trans. Assoc. Am. Phys.* (1962) 75:307–320.

Horne, D.W. and Patterson, D., "*Lactobacillus casei* microbiological assay of folic acid derivatives in 96–well microtiter plates," *Clin. Chem.* (1988) 34:2357–2359.

Jones, P. et al., "Interpretation of serum and red cell folate results. A comparison of microbiological and radioistopic methods," *Pathology* (1979) 11:45–52.

Kohashi, M. et al. "Microdetermination of folate monoglutamates in serum by liquid chromotography with electrochemical detection," *J. Chromatogr.* 382:303–307, 1986.

Labadarious et al., "Gas chromatographic analysis of amino acids in physiological fluids: a critique," *J. Chromatography* (1984) 310:223–231.

Lashner, B.A., "Red blood cell folate is associated with the development of dysplasia and cancer in ulcerative colitis," *J. Cancer Res, Clin. Oncol.* (1993) 119:549–554.

Levine, S., "Analytical inaccuracy for folic acid with popular commercial vitamin $B_{12}$/folate kit," *Clin. Chem.* (1993) 39:2209–2210.

MRC Vitamin Study Research Group, "Prevention of neural tube defects: results of the medical research council vitamin study," *Lancet* (1991) 338:131–137.

Noronha, J.M. and Silverman, M., "On folic acid, vitamin $B_{12}$, methionine and formiminoglutamic acid metabolism," 2. Europäisches Symposion über Vitamin $B_{12}$ und Intrinsic Factor, Hamburg 2.–5. Aug. 1961, pp. 728–736.

Nussbaum, R.L. and Ledbetter, D.H., "The fragile X syndrome," In *The Metablolic Basis of Inherited Diseases*, (Scriver, C.R. et al., Eds.) McGraw Hill New York, NY (1989) pp. 327–341.

Plante, L.T. et al., "Preparation of folic acid specifically labeled with carbon–13 in the benezoyl carbonyl," *Methods Enzymol.* 66:533–538, 1980.

Priest, D.G. and Doig, M.T., "Tissue folate polyglutamate chain length determination by electrophoresis as thymidylate synthase—flurodeoxyuridylate ternary complexes," *Methods Enzymol.* 122:313–332, 1986.

Rice, E.W. Rapid determination of total hemoglobin as hemiglobin cyanide in blood containing carboxyhemoglobin, *Clin. Chim. Acta* (1967) 18:89–91.

Savage et. al., "Sensitivity of serum methylmalonic acid and total hemocysteine determinations for diagnosing cobalamin and folate deficiencies," *Am. J. Med.* (1994) 96:239–246.

Selhub, J. et al., "Preparation and use of affinity columns with bovine milk folate–binding protein (FBP covalently linked to sepharose 4B," *Methods Enzymol.* (1980) 66:686–90.

Shahrokhi, F. and Gehrke, "Quantitative gas–liquid chromatography of sulfur containing amino acids," *J. Chromatography* (1968) 36:31–41.

Shane B., "Identification of folylpoly(γ–glutamate) chain length by cleavage to and separation of ρ–aminobenzoylpoly(γ–glutamates)," *Methods Enzymol.* (1986) 122:323–330.

Shiota, T., Enzymic synthesis of folic acid–like compounds by cell–free extracts of *Lactobacillus arabinosus*, *Archives of Bioch.* (1959) 80:155–161.

Shrovan et al., "The neuropsychiatry of megaloblastic anaemia," *British Medical J.* (1980) 281:1036–1038.

Smith, R.G. et al., "Mass spectrometry of permethylated folic acid analogs," *Biomed. Mass Spectrom.* (1981) 8:144–148.

Stokstad, E.L.R. and Koch, J., "Folic acid metabolism," *Physiol. Rev.* (1967) 47:83–116.

Tamura, T., "Microbiology assay of folates," In *Folic Acid Metabolism in Health and Disease*, (Picciano, M.F. et al., Eds.) Wiley–Liss, Inc., New York, NY, pp. 121–137, 1990.

Tamura, T. et al., "*Lactobacillus casei* response to pteroylpolyglutamates," *Anal. Biochem.* (1972) 49:517–521.

Temple Jr. C, Elliott RD, Rose JD, Montgomery JA. *J. Med.Chem.* (1979) 22:731 (Abstract Only).

Varela–Moreiras, G. et al., "Combined affinity and ion pair liquid chromatographics for the analysis of folate distribution in tissues," *J. Nutr. Biochem* (1991) 2:44–53.

Temple,C. Jr. et al., "Preparation and Purification of L–(±–5–Formyl–5,6,7,8–tetrahydrofolic Acid," *J. Medicinal Chem* (1979) 2(6):731–734.

GAS CHROMATOGRAPHY/MASS SPECTROMETRIC DETERMINATION OF FOLIC ACID COENZYMES

This is a continuation of application Ser. No. 08/347,855, filed on Dec. 1, 1994 now abandoned.

This invention was made at least in part with funding from the National Institutes of Health (award #1F 32-HD07647) and from the Veterans Administration Hospital (RAGS award #0001). Accordingly, the United States Government may have certain rights in this invention.

BACKGROUND OF THE INVENTION

(1) Field of the Invention

This invention pertains in general to methods for quantifying folate coenzymes in a sample by gas chromatography/mass spectrometry using stable isotope labeled internal standards and in particular to quantitation in biological fluids such as blood, serum, urine, amniotic fluid or cerebrospinal fluid.

(2) Description of Prior Art

Folic acid, one of the commonly consumed vitamins during pregnancy, is the prototype of the folate family of B-vitamins (Scheme I). Folates exist in tissues as at least eight different coenzyme forms and are needed for different metabolic reactions in the body (Brody, T. et al., In *Handbook of Vitamins* (Machlin, L. J. Ed.), Marcel Dekker, Inc., New York, N.Y. (1984) pp. 459–496). Prolonged deficiency of folate vitamins result in a condition called megaloblastic anemia (Herbert V., Trans. Assoc. Am. Phys. (1962) 75:307–320), which is completely reversed by treatment with folate. Subclinical folate deficiency or disorders of folate metabolism have been implicated in the pathogenesis of a variety of disorders ranging from neurological and psychiatric disorders (Botez, M. I. et al., Can. Med. Assoc. J. (1976) 115:217–223; Godfrey, P. S. A. et al., Lancet (1994) 336:393–395; Nussbaum, R. L. and Ledbetter, D. H., In *The Metabolic Basis of Inherited Diseases* (Scriver, C. R. et al., Eds.) McGraw Hill, New York, N.Y. (1989) pp. 327–341; CDC (1992) MMWR 41, RR14, 1–7) to development or promotion of cancer (Lachner, B. A., J. Cancer Res. Clin. Oncol. (1993) 119:549–554; Harper, J. M. et al., Acta Cytol. (1994) 38:324–330). Folate supplementation during the periconceptual period (the period around the time of conception) to mothers has been shown to prevent the occurrence of neural tube defects in babies (MRC Vitamin Study Research Group, Lancet (1991) 338:131–137).

Measurement of serum or red blood cell folates is considered essential in the investigation of several types of anemias (Herbert V., Trans. Assoc. Am. Phys. (1962) 75:307–320). Serum folate levels reflect the current folate status in serum and can be altered by consumption of even a single meal rich in folates. Red blood cell (RBC) folate reflects the folate status in tissues for the preceding 3–4 months as the median life-span of a RBC is approximately 90 days. RBC folate measurements are, therefore, considered better indicators of folate deficiency than serum folates (Herbert V., Trans. Assoc. Am. Phys. (1962) 75:307–320; Babior, B. M., In *Hematology* (Williams, W. J. et al. Eds.) McGraw Hill, New York, N.Y. (1990) pp. 339–355).

Several methods have been described for estimation of the relative folate content in a biological sample. However there is no reference method to measure the total amount of folate in a sample and there are no published methods for measurement of different folate coenzymes from a blood sample (Hansen, S. I. et al., Clin. Chem. (1987) 33:1360–1363). Furthermore, all currently used methods of folate measurement suffer from problems of sensitivity, specificity and accuracy (Levine, S., Clin. Chem. (1993) 39:2209–2210; Gunter, E. W. and Twite, D. B., Clin. Chem. (1990) 36:2139; Gilois, C. R. and Dunbar, D. R., Med. Lab. Sci. (1987) 44:33–40; Brown, R. D. et al., Pathology (1990) 22:82–87; Jones, R. et al., Pathology (1979) 11:45–52; Dawson, D. W. et al., J. Clin. Pathol. (1987) 40:393–397).

The methods of measurement of total folates in current use include radio-isotope methods, microbiological methods and high pressure liquid chromatography (HPLC) based methods. All the reported methods estimate the total folate content of a sample by comparing activity to a standard curve generated using a single folate coenzyme as the standard in a separate assay (Fleming, A. F. et al., Am. J. Clin. Nutr. (1971) 24:1257–1264; Horne, D. W. and Patterson, D., Clin. Chem. (1988) 34:2357–2359; Tamura, T. In *Folic Acid Metabolism in Health and Disease*, (Picciano, M. F. et al., Eds.) Wiley-Liss, Inc., New York, N.Y., pp. 121–137). For example, in the most commonly used method of folate analysis, i.e. the radioisotope competitive binding assay (RIDA), the folate content of a sample is calculated by comparing binding to a standard curve generated using folic acid or 5-methyl tetrahydrofolate as an external standard. Patents relating to radioassays include U.S. Pat. Nos. 4,276,280, 4,247,453, 4,091,087 and 3,989,812. In the microbiological assay, microorganisms requiring folates for growth are grown in the presence of a sample containing folates and compared to growth of a similar set of microorganisms in the presence of a standard. In HPLC based methods, the identification of folates is based on synchronization of retention times, spiking of samples with markers or a combination of those strategies (Varela-Moreiras, G. et al., J. Nutr. Biochem (1991) 2:44–53).

These methods are adequate for measurement of a sample containing predominantly a single coenzyme form such as human serum. However, when applied to measure RBC folates or samples with a mixture of different folate coenzymes these methods become inaccurate for the following reasons: (1) folates exist as at least eight different coenzyme forms in cells and different coenzymes have different affinities for folate binding protein (Stokstad, E. L. R., Physiol. Rev. (1967) 47:83–116) which is used in limiting amounts in the radio-isotope assay; (2) polyglutamate chain length affects the affinity of folate to the binding protein (Tamura, T. et al., Anal. Biochem. (1972) 49:517–521); (3) folate monoglutamate standard used in the radioisotope assay is a pure folate and therefore ignores the variabilities of different interactions in a biologic sample; and (4) growth characteristics of microorganisms used in microbiologic assays are different for different folate coenzymes. The use of mass spectroscopy to measure materials in biological fluids using deuterated internal standard compounds is described in U.S. Pat. No. 5,124,267. See also U.S. Pat. No. 5,012,052. U.S. Pat. No. 4,135,880 describes a folate assay with ion-exchange resin bound-free separation.

Though a variety of illnesses are thought to be associated with subclinical deficiency or disorder of folate metabolism, because of the above technical limitations of the assay methods, the exact folate levels in biological fluids of patients is not known. Thus, there is a need in the art for a specific, sensitive and accurate assay for the determination of total folates and different coenzymes in biological and other samples.

As folates exist in tissues as different coenzyme forms with different polyglutamate chain lengths, a system which measures, on a mole for mole basis, something common to all different folate coenzyme forms will yield the total folate content in a biological sample. A system which can separate different coenzymes will yield information regarding the mix of different coenzymes in a sample. We have devised new methods to answer these problems.

SUMMARY OF THE INVENTION

The subject method comprises a gas chromatography/mass spectrometry (GC/MS) method for the determination of total and individual pools of folate coenzymes in a biological sample. All folate coenzymes have the parent structure of a paraminobenzoic acid molecule linked to a pteridine ring in a C9—N10 linkage at the amino end and one or more glutamic acid molecules attached at the carboxyl end (see Formula I). One-carbon substitutions can occur at the 5 or 10 positions with methyl or formyl groups or a methylene or methenyl bridge formation between the 5 and 10 positions. The glutamic acid moieties may vary from one to many, linked at the α-carboxyl in a chain formation.

said purified in vitro body fluid by GC/MS analysis; and, (4) determining the in vivo concentration of said folate pools by correcting the quantitated in vitro endogenous concentration for endogenous loss as reflected by the loss in said known amount of said internal standard.

The different folate coenzymes can be separated by means known to the art and as described herein and quantified by the methods of this invention.

Biological samples in which total folates and folate pools can be measured include whole blood or serum as exemplified here as well as urine, cerebrospinal fluid and amniotic fluid. These samples may be of human origin or they may be taken from animals other than humans. Additionally, the subject method can also be used to quantitate the folate composition of biological materials of any source including foodstuffs or folate-containing samples from any source, as will be apparent to those skilled in the art. Preferably the internal standard is a non-radioactive heavy isotope of the substances to be measured, which is advantageous in that through mass spectrometry it provides more accurate mea-

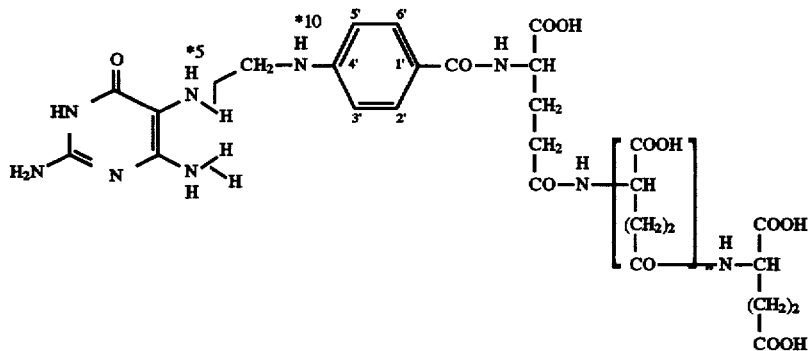

I

Said folate coenzymes include three different pools, each pool consisting of different coenzymes. The different pools have been designated such by previous investigators based on acid/base reactivity of the folate coenzymes. Pool 1 consists of tetrahydrofolate, dihydrofolate and 5,10-methylenetetrahydrofolate. Pool 2 consists of 5-methyltetrahydrofolate only. Pool 3 consists of 5-formyltetrahydrofolate, 10-formyltetrahydrofolate, 5,10-methenyltetrahydrofolate and 5-formiminotetrahydrofolate. The said pools of folates may be of different polyglutamate chain length as mentioned above. The co-enzymes may be separated by means known to the art such as, for example, as described herein and in Eto, I. and Krumdieck, C. L., "Determination of Three Different pools of Reduced One-carbon-substituted Folates," Anal. Biochem. (1980) 109:167–184.

The methods disclosed herein are more sensitive and specific than prior art methods and have the additional advantage of providing the composition of different folate pools in a biological sample. Furthermore, the folates can be unambiguously identified when assayed together with stable isotope-labeled internal standards and any loss of endogenous folate during sample preparation can be corrected for.

The subject method for determination of the in vivo concentration in blood or other body fluid of total or one or more pools of folate listed above comprises the steps of: (1) combining a known amount of folate internal standard with a biological sample collected in vitro, said biological sample containing at least one of the different folate pools; (2) at least partially purifying said endogenous and internal standard folates from other compounds in said in vitro body fluid; (3) quantitating said folate pools' concentrations in surement than radio-labeled substances and in that non-radioactive isotopes are safe for the environment. Preferably the internal standard is a stable isotope compound which behaves identically to the compounds to be measured. A preferred internal standard for use in the GC/MS methods for analysis of a mixture of folates present in a biological sample is a mixture of stable isotope-labeled folates, preferably the label being $^{13}C$ substitutions for all six carbon atoms of the benzene ring of the paraaminobenzoic acid moiety present in each folate molecule. The structures of a number of different folate coenzymes are given below in Formulas II-IX:

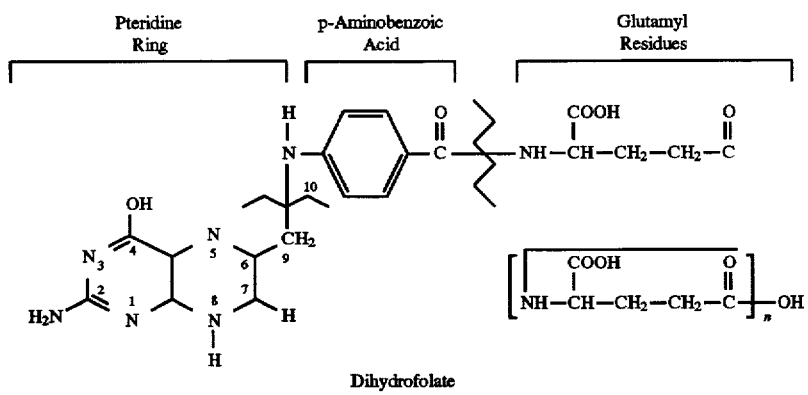
Dihydrofolate     II
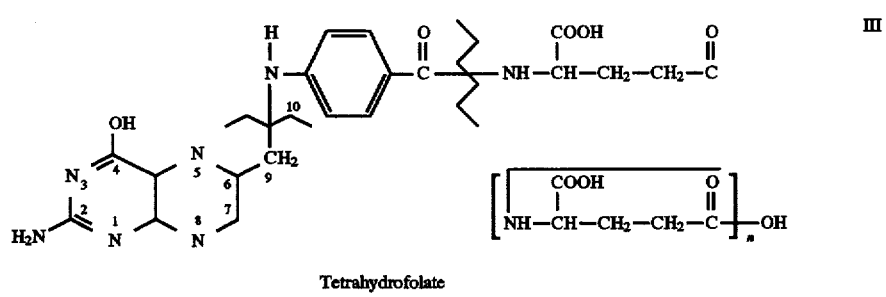
Tetrahydrofolate     III
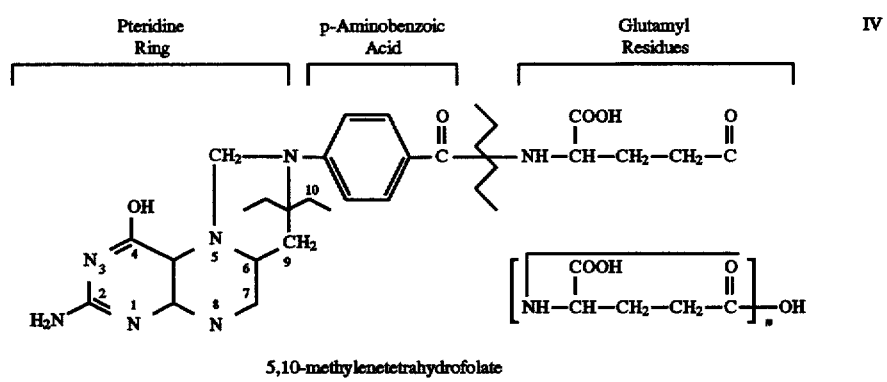
5,10-methylenetetrahydrofolate     IV
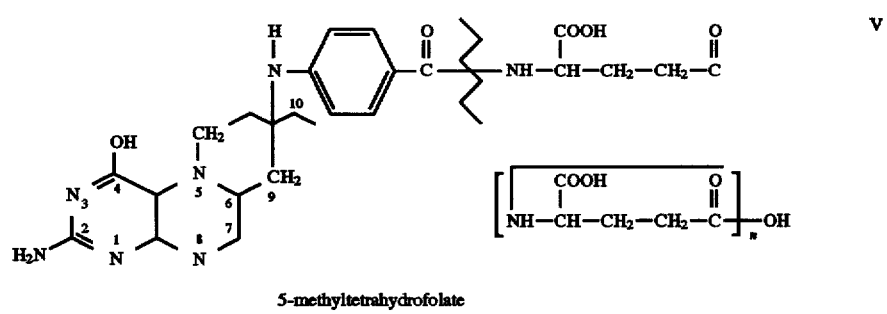
5-methyltetrahydrofolate     V
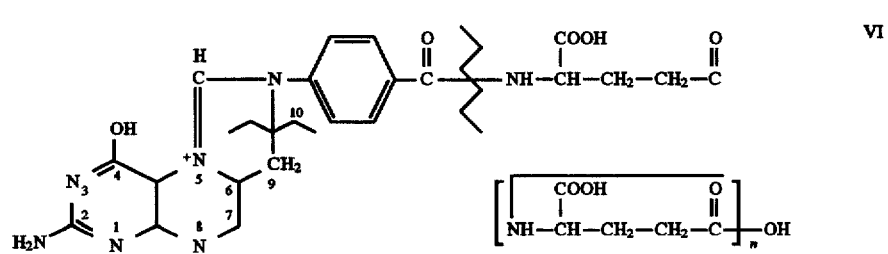
5,10-methenyltetrahydrofolate     VI -continued

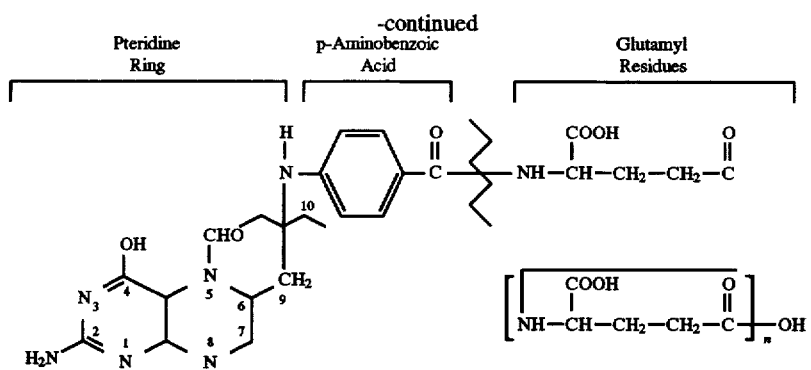

5 formyltetrahydrofolate

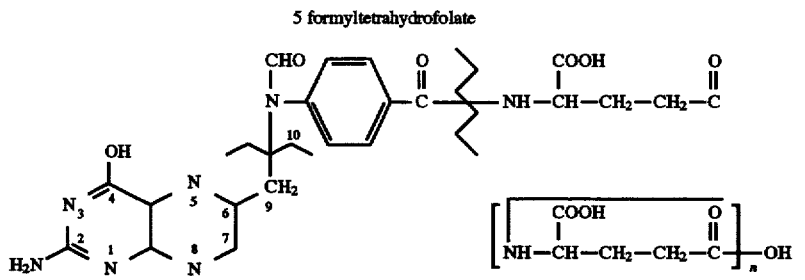

10-formyltetrahydrofolate

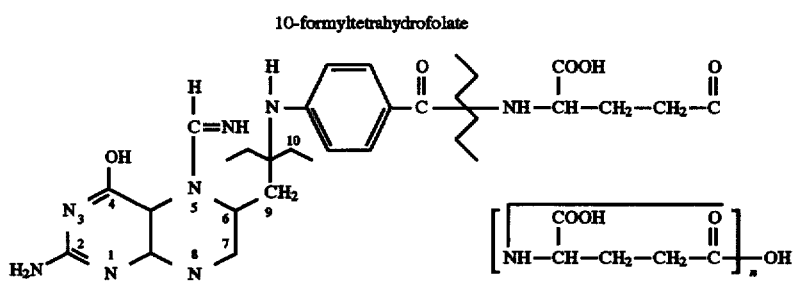

5-forminiminotetrahydrofolate

The parent folic acid (pteroylglutamic acid) molecule is not metabolically active. Biologically important folate coenzymes are produced in the body by enzymatic reactions, as shown in FIG. I (Brody, T. et al., in *Handbook of Vitamins*, (Machlin, Z. J. Ed) Marcel Dekker, Inc., New York, N.Y. (1984) pp 459–496).

Deviations from normal levels of folate coenzymes are associated with several disorders, particularly those resulting from deficiency of any one of the several enzymes for which folate coenzymes are needed as cofactors.

Abnormality of folates is usually a decrease from the accepted normal range. However an increased level may result in precipitation of seizures in persons on anticonvulsant medication. Furthermore, increased levels in patients with untreated vitamin $B_{12}$ deficiency may accelerate the development of neurological symptoms. Altered levels of folates could be in red blood cells, serum, cerebrospinal fluid, amniotic fluid or any body tissues. Measurement of levels of one or more pools of folates in patients suspected of a deficiency in one of the enzymes which needs folates can be used in the diagnosis of such disorders. Similarly measurement of folate coenzymes can allow the clinician to monitor the course of treatment with a return to normal range of a particular coenzyme pool indicative of successful treatment.

This invention also comprises a method, herein called Reverse Ion Phase Affinity Chromatography (RIPAC), for purifying or separating a selected or desired component from a biological fluid. The component must be capable of binding to a binding protein having a molecular weight larger than other components of said fluid. Preferably the binding protein has a molecular weight higher than all or most of the other components of said fluid. The binding protein preferably has a molecular weight of at least about 3,000 Daltons, and more preferably at least about 10,000 Daltons. The binding agent must have the following properties: (1) is capable of staying in solution during the binding period; and (2) does not bind to the ion exchange agent.

The term "component" refers to a single chemical entity or to a group of entities which are all capable of binding to the binding agent. Preferred components include folates, cobalamin, retinoids, and steroids.

The desired component is bound to an ion exchange agent (anionic or cationic), preferably a strong ion exchange agent on a support. A strong ion exchange agent used with a specific binding agent will optimize separation of the desired component.

The bound component on the ion exchange agent is then contacted with a liquid medium comprising the binding agent so that the component is extracted from the ion exchange agent into the liquid medium. The binding agent is allowed to contact the ion exchange agent for a sufficient amount of time to effect binding of the desired component to the binding agent. As will be appreciated by those skilled in the art, increasing temperature and/or binding agent concentration will improve process efficiency. A preferred temperature is 37° C. The affinity of the binding agent for the desired component should be high enough to effect removal from the ion exchange agent, preferably at least about $K = \geq 10^{-7}$. The affinity of the binding agent for the desired component need not necessarily be greater than the affinity of the ion exchange agent for the desired component, so long as the difference in affinities can be compensated for by using a high concentration of binding agent. Suitable liquid media for carrying the binding agent are water and polar or nonpolar organic solvents.

The binding agent may be any composition known to the art capable of specifically binding the desired component, staying in solution during the binding period, and not binding to the ion exchange material. Binding agents may be proteins, lectins, chelating agents, nucleotide sequences or antibodies. Solid phase binding agents can also be $C_{18}$ or charcoal. In a preferred embodiment, when the desired component is the class of folates, a preferred binding agent is folate binding protein. When the desired component is vitamin $B_{12}$, the preferred binding agent is one of the $B_{12}$ binding proteins. When the desired component is thyroxine, the preferred binding protein is thyroxine binding globulin. As will be appreciated by those skilled in the art, other binding proteins and components to which they bind may be used in the present method.

The desired component is then separated from the binding agent. In a preferred embodiment, the liquid medium containing the binding agent and desired component is filtered through a filter designed to capture or retain the bound component and binding agent and allow the remainder of the liquid and components to pass through. If the binding agent is not the largest molecular weight component of the biological fluid, additional components may be retained on the filter and are separated by means known to the art, such as further filtration, ion exchange and hydrophobic chromatography. The desired component is then separated from the binding agent such as by cleaving by means known to the art, followed by separation, e.g., by ion exchange chromatography or other means known to the art.

In a preferred embodiment hereof wherein the desired component is folate, the RIPAC folate separation method is part of a method of measuring total or selected folates in a biological fluid by gas chromatography/mass spectroscopy (GC/MS) using an internal standard and the component to be separated is the entire class of folates, including co-enzymes contained in the biological fluid and folate co-enzyme(s) added for use as an internal standard.

The present invention also provides a method for making a mixture of non-radioactively-labeled stable isotope folate co-enzymes.

The term "non-radioactively-labeled" refers to substitution of one or more atoms of a compound with a non-radioactive isotope of the atom(s). Preferred isotopes of such atoms are $^2H$, $^{13}C$, $^{15}N$ and $^{18}O$.

The term "stable isotope" as used herein with respect to a compound means that the isotopic atom is substantially stable in said compound under the metabolic procedures described herein and is not significantly replaced by the natural form of the atom. The stable isotopes used in this invention are non-radioactive isotopes.

Folate co-enzymes comprise, but are not limited to, tetrahydrofolate, dihydrofolate, 5,10-methylenetetrahydrofolate, 5-methyltetrahydrofolate, 5-formyltetrahydrofolate, 10-formyltetrahydrofolate, 5,10-methenyltetrahydrofolate, and 5-formiminotetrahydrofolate.

The method involves use of Lactobacillus arabinosus to synthesize the co-enzymes from non-radioactively-labeled stable isotope para-aminobenzoic acid (PABA). Lactobacillus arabinosus are known to synthesize folates when grown on a medium containing PABA. See, e.g., T. Shiota, "Enzymic Synthesis of Folic Acid-Like Compounds by Cell-Free Extracts of Lactobacillus arabinosus, Archives of Bioch. (1959) 80:155–161. Applicants have discovered that this organism will synthesize a mixture of isotopically-labeled folate co-enzymes comprising the above-named molecules by incorporating labeled PABA added to the medium.

The method involves providing a suitable growth medium for the Lactobacillus arabinosus as known to the art, e.g., a medium comprising vitamin-free casamino acids (Difco), 5 g; sodium acetate.$3H_2O$ and glucose, 10 g each; $K_2HPO_4$ and $KH_2PO_4$, 0.5 g each; L-cysteine-HCl, 0.2 g; DL-tryptophan, 0.3 g; ammonium chloride, 3 g; adenine, guanine and uracil, 10 ng each; riboflavin, nicotinic acid, pyridoxal, biotin, 5 µg; salts B, 5 ml; water 1000 ml; at pH 6.8. To this medium is added 10 µg non-radioactive isotopically-labeled PABA. Preferably the labeled PABA is $^{13}C_6$-PABA in which all six carbons of the benzene ring are substituted with $^{13}C$. Other isotopes of PABA useful in this process are $[^2H]$-PABA, $[^{15}N]$-PABA, $[^{17}O]$- or $[^{18}O]$-PABA, or combinations thereof. Such isotopes are described in U.S. patent application Ser. No. 08/345,534, a continuation of Ser. No. 08/053,545, now U.S. Pat. No. 5,506,147, incorporated herein by reference.

The bacteria are then grown, preferably to confluency, with regrowth on fresh culture medium, harvested preferably by centrifugation, and folates recovered from cell lysates by means known to the art.

In a preferred embodiment hereof the recovered folates are used as the internal standard in the method of measuring total folates in a biological fluid by GC/MS described herein. For this use, the folate co-enzymes do not need to be completely purified from the cell lysates. As described in the examples hereof, the folate co-enzymes are recovered from frozen bacteria by treatment with 2-mercaptoethanol at pH 9.6, heated to about 102° C., then centrifuged to recover a supernatant containing the co-enzymes. The supernatant can be added to the biological fluid being tested without further treatment, as described herein.

Alternatively, the co-enzymes are purified by RIPAC as described above, then separated by the differential cleavage method described herein and used separately as internal standards for GC/MS quantitation of the same specific co-enzyme in a biological fluid.

BRIEF DESCRIPTION OF THE DRAWINGS

FIGS. 2A, 2B and 2C show, respectively, the total ion chromatograms of pure double-derivatized PABA; of $^{13}C_6$-PABA; and of $^2H_2$-PABA.

DETAILED DESCRIPTION OF THE INVENTION

Figure 1:
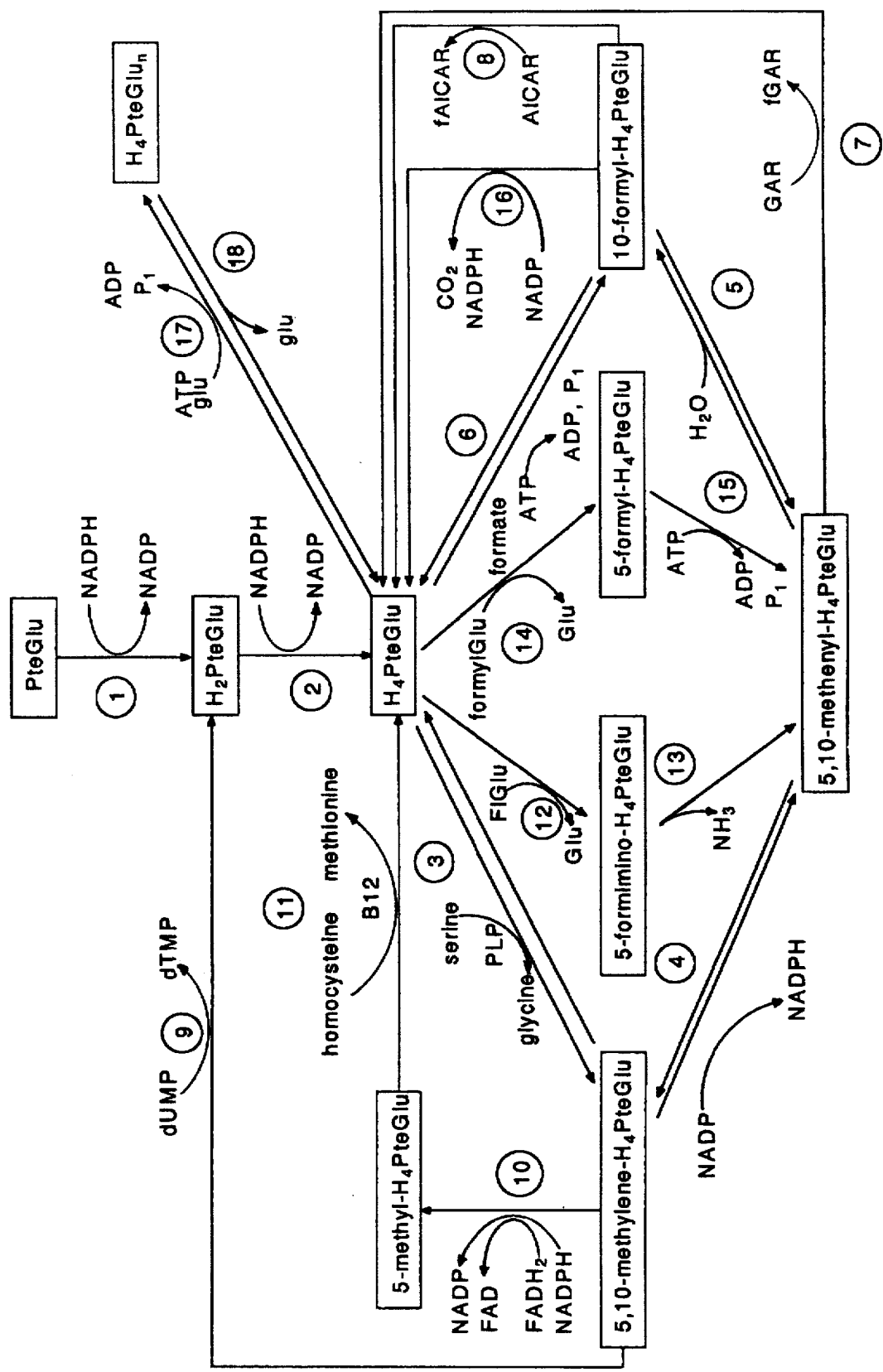
FIG. 1 is a scheme depicting folate-mediated reactions in 1-carbon metabolism. The numbers refer to reactions catalyzed by the following respective enzymes: (1) dihydrofolate reductase; (2) dihydrofolate reductase; (3) serine transhydroxymethylase; (4) 5,10-methylenetetrahydrofolate dehydrogenase; (5) 5,10-methenyltetrahydrofolate cyclohydrolase; (6) 10-formyltetrahydrofolate synthetase; (7) glycinamide ribotide formylase; (8) aminoimidazole carboxamide ribotide formylase; (9) thymidylate synthetase; (10) 5,10-methylenetetrahydrofolate reductase; (11) methionine synthetase; (12) tetrahydrofolate formiminotransferase; (13) formiminotetrahydrofolate cyclohydrolase; (14) glutamate transformylase; (15) formyl-tetrahydrofolate isomerase; (16) 10-formyltetrahydrofolate dehydrogenase; (17) folate polyglutamate synthetase; and (18) γ-glutamylhydrolase. In mammals, reactions 12 and 13 are catalyzed by a single bifunctional enzyme and reactions 4, 5 and 6 are catalyzed by a trifunctional enzyme. The various abbreviations mean: dUMP, deoxyuridine monophosphate; dTMP, deoxythymidine monophosphate (thymidine monophosphate); PLP, pyridoxal phospate; FiGlu, formiminoglutamic acid; fAICAR, formyl-aminoimidazole carboxamide ribonucleotide; AICAR, aminoimidazole carboxamide ribonucleotide; GAR, glycinamide ribonucleotide; fGAR, formylglycinamide ribonucleotide; and $B_{12}$, vitamin $B_{12}$.

The subject invention provides a method of accurately determining the in vivo concentrations of total folates or one or more different pools of folates with correction for loss of endogenous folates during sample storage and/or preparation. The GC/MS method described herein is more sensitive and specific than existing methods. The use of internal standards enables the determination of any potential loss of the endogenous folates during sample processing.

Folates belong to a group of compounds comprising the common general structure of a pteridine ring attached to a paraaminobenzoic acid to which a one or more glutamic acid side chains are attached (see Formula I). Structural differences in the different folate coenzymes may result from substitution of one-carbon fragments at position 5 or 10 or result from differences in oxidation states in the pteridine ring. Further, the number of glutamic acid molecules in the side chain could vary from one to ten for a particular folate coenzyme. Three different folate pools are known in prior art based on differences in acid and oxidative cleavage of the C9—N10 bond connecting the pteridine ring to the paraaminobenzoic acid moiety of a folate molecule. Pool 1 consists of tetrahydrofolate, dihydrofolate and 5,10-methylenetetrahydrofolate. Pool 2 consists of 5-methyltetrahydrofolate only. Pool 3 consists of 5-formyltetrahydrofolate, 10-formyltetrahydrofolate, 5,10-methenyltetrahydrofolate and 5-formiminotetrahydrofolate.

The internal standard is any suitable compound which will behave substantially identically with the endogenous target compound throughout the procedure in analysis on the mass spectrometer, but which is distinguishable under mass spectrometric analysis and can be separately and simultaneously measured. The internal standards should be sufficiently similar to the target compounds to be effectively chemically identical to the target compounds for the purposes of the assay. Examples of preferred internal standards for purposes of this assay are folates with substitution of all six carbons on the paraaminobenzoic acid moiety with $^{13}C$. Other suitable compounds can have substitution of nitrogen of the paraaminobenzoic acid moiety with $^{15}N$, substitution of the oxygen of the paraaminobenzoic acid moiety with $^{18}O$, or substitutions of hydrogens at positions 2 and 6 of the paraaminobenzoic acid moiety with [$^2H_2$]. Compounds suitable for use as internal standards can be prepared by the methods of U.S. Pat. No. 5,506,147, incorporated herein by reference.

Quantification is based on the assumption that the ratio of measured target compound to measured internal standard is proportional to the ratio of the total unknown target compound in the initial sample to the internal standard in the initial sample. This assumes that the same recovery rate for both target compounds and the internal standards exist. In quantitation, no special correction for natural isotopic abundance of stable isotopes is used since a $^{13}C_6$-PABA-containing internal standard is used. The contamination of one isotope by the other, when a mixture of $^{12}C$ and $^{13}C$-PABA is measured, is less than 0.2%. The prepared internal standard used in the assay is >99.5% enriched with $^{13}C$. The prepared internal standards are kept as liquid at −20° C., protected from light.

Optionally, it may be necessary or desirable to purify the target compounds and internal standards before analysis. Any means known to the art for the purification and separation of small molecular weight substances, e.g., anion or cation exchange chromatography, gas chromatography, liquid chromatography or high pressure liquid chromatography may be used. Methods of selecting suitable separation and purification techniques and means of carrying them out are known in the art (see, e.g., Labadarious et. al., J. Chromatography (1984) 310:223–231, and references cited therein; and Shahrokhin and Gehrke, J. Chromatography (1968) 36:31–41). It is preferred that folates are at least partially purified from samples before derivatization using a combination of affinity chromatography, and anion and cation exchange chromatography.

Optionally, it may be necessary or desirable to modify the target compound and the internal standard to alter or improve certain characteristics to facilitate purification and/ or separation. This practice is well known in the art as derivatization, e.g., it may be desired to convert the target and reference compounds to analogs having improved solubility, increased volatility, different mass to charge ratio, etc. to facilitate purification and or separation and identification for analysis on the GC/MS (see, e.g., D. R. Knapp, Handbook of Analytical Derivatization Reactions, (1979) John Wiley & Sons, New York). A preferred procedure is propionation or acetylation of the purified PABA prior to derivatization using tert-butyldimethylsilyltrifluoroacetamide (MTBSTFA) derivatives to facilitate separation and identification on a combined GC/MS apparatus. Means and methods of silylating compounds for this purpose are known in the art, (see, e.g., Knapp, supra; Bierman et. al., J. Chromatography (1986) 357:330–334). A preferred method involves combining the target compounds with internal standards, specifically purifying the folates and subsequently cleaving the folates to individual PABA molecules, incubating the purified PABA with propionic anhydride, drying and incubating the propionated PABA in a mixture of acetonitrile and MTBSTFA. The resulting silylated target and reference compounds are then analyzed using the GC/MS.

Combined GC/MS analysis, by combining a separation technique with an analytical technique, has the advantage of unambiguously identifying PABA and $^{13}C_6$-labeled PABA by simultaneous measurement of different derivatives which have different masses. Additionally the GC/MS combined analysis method can be automated to reduce processing time, labor and material costs.

Figure 2A:
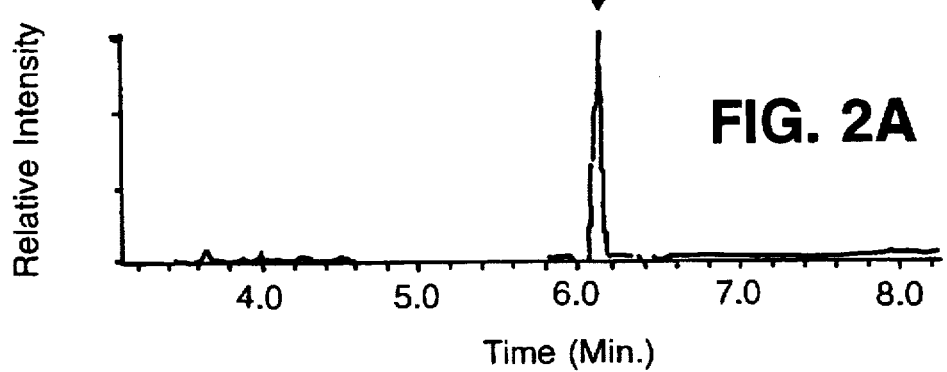
FIGS. 2A–2C illustrate total ion chromatogram of paraaminobenzoic acid, purified from a mixture of stable isotope labeled folate internal standard and 100 μl of whole blood, derivatized initially with propionic anhydride and subsequently with tertbutyldimethyl-silyltrifluoroacetamide (MTBSTFA).
Figure 2B:
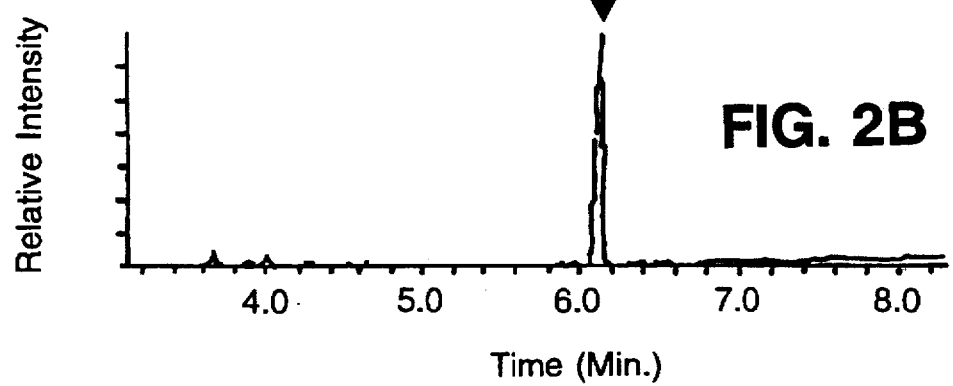
Figure 2C:
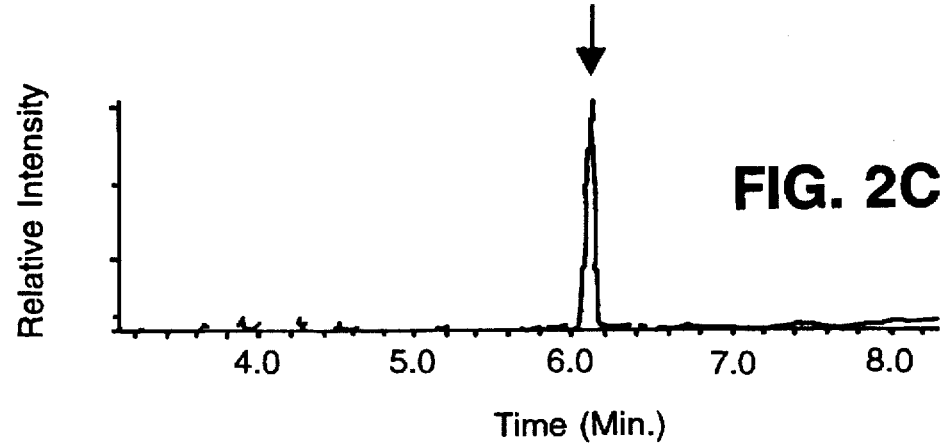
Figure 3A:
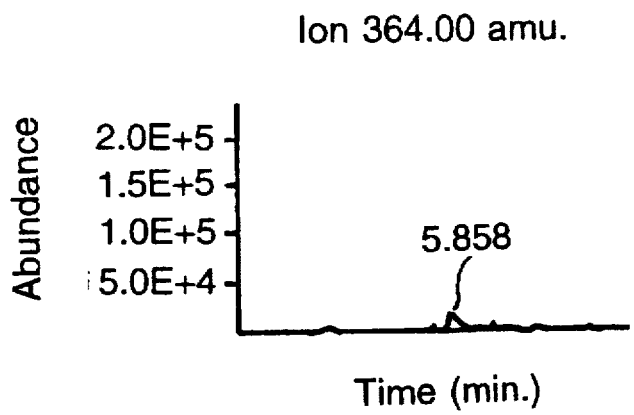
FIGS. 3A–3D illustrate SIM chromatograms (m/z 150–650) of MTBSTFA derivatized propionyl PABA, [$^{13}C_6$] propionyl PABA and [$^2H_2$] propionyl PABA.
Figure 3B:
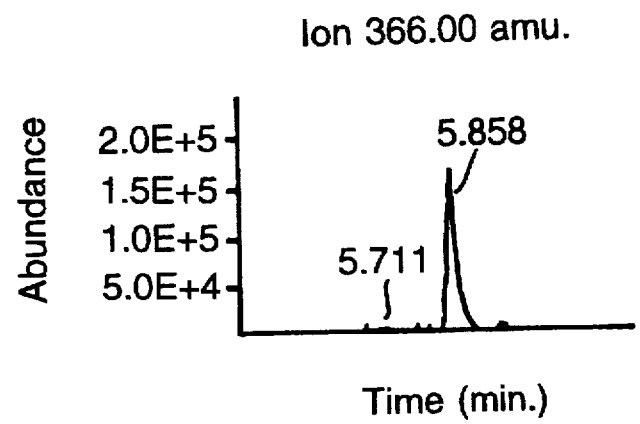
Figure 3C:
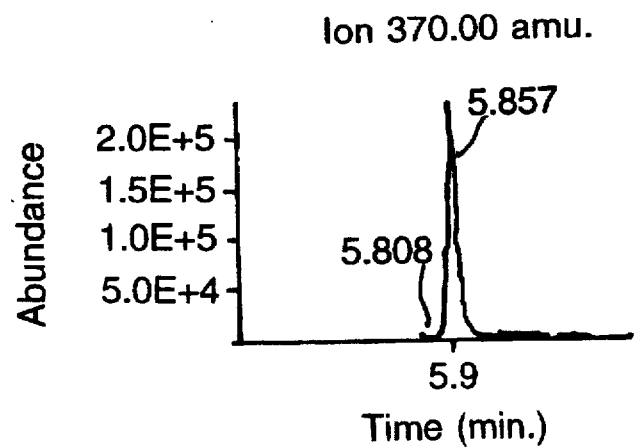
Figure 3D:
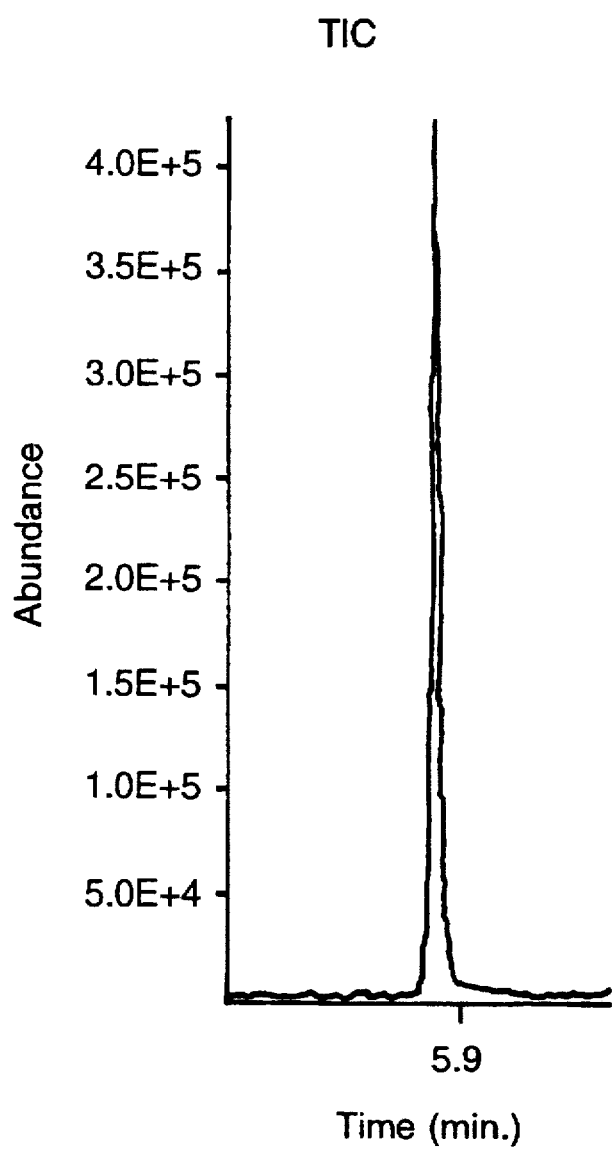

The total ion chromatograms of pure double-derivatized PABA, $^{13}C_6$-PABA and $^2H_2$-PABA are shown in FIGS. 2A–2C. All three compounds elute at 6.29 minutes. All compounds yielded single major peaks. Based on the structure of PABA and possible derivatization sites, masses of PABA and the potential MTBSTFA derivatives and the M-57$^+$ ions are calculated according to standard methods. These values are displayed in Table 1.

TABLE 1

Figure 4A:
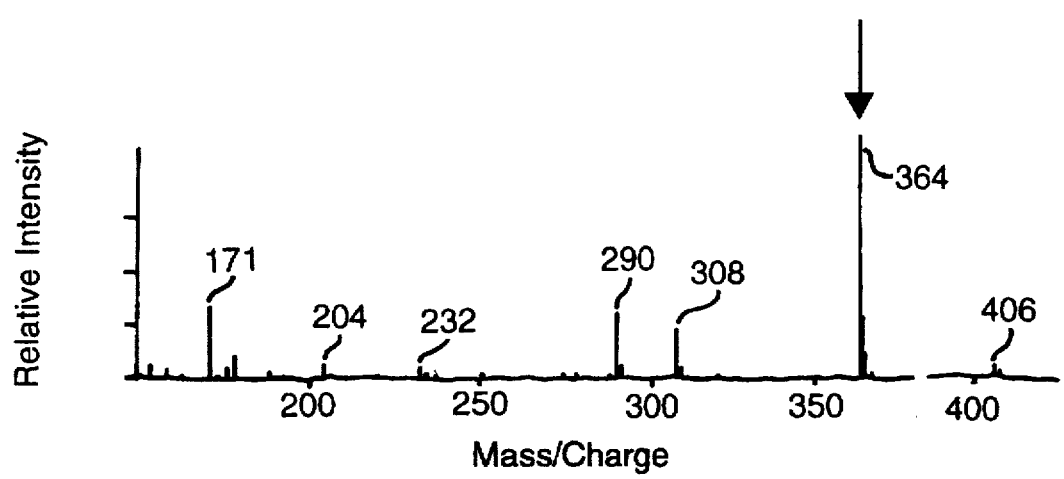
FIGS. 4A–4C illustrate the mass spectra of MTBSTFA derivatized compounds generated for (A) propionyl PABA, (B) [$^{13}C_6$] propionyl PABA and (C) [$^2H_2$] propionyl PABA. [M-57$^+$] m/z of each of the derivatives is indicated by an arrow in the figure.
Figure 4B:
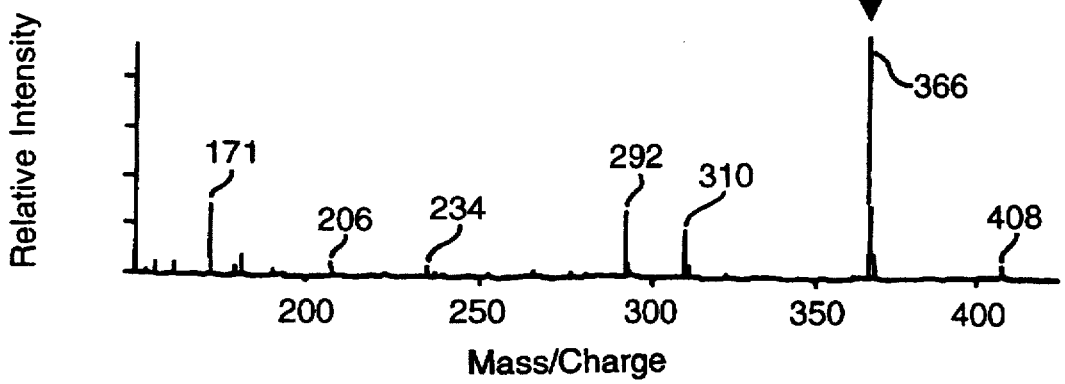
Figure 4C:
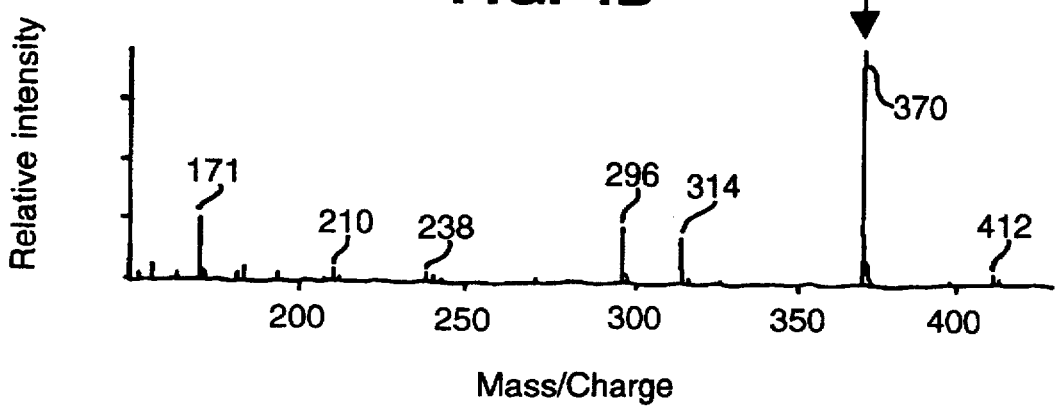

Proposed structure of ions generated from MTBSTFA-derivatized propionated p-aminobenzoic acid, [$^2H_2$]p-aminobenzoic acid and [$^{13}C_6$]p-aminobenzoic acid shown in FIGS. 4A–4C

| | |
|---|---|
| 421/423/427 | M$^+$, the total mass of derivatized products |
| 406/408/412 | loss of methyl group from either of derivatized groups, NH$_2$ or COOH, generating the ion, without loss from parent molecule |
| 364/366/370 | loss of tert-butyl group from either of derivatized groups, NH$_2$ or COOH, generating the ion, without loss from parent molecule |
| 308/310/314 | loss of tert-butyl group from either of derivatized groups, NH$_2$ or COOH from M+ of non-propionated PABA |
| 290/292/296 | loss of entire tert-butyldimethylsilyl group and O of carboxyl group at carboxyl derivatization site. |
| 232/234/238 | loss of entire tert-butyldimethylsilyl group, carboxyl group and a methyl group |
| 204/206/210 | loss of entire tert-butyldimethylsilyl group and loss of O at carboxyl group, loss of tert-butyl group at derivatized NH$_2$ and loss of ethyl group from propionated site |

Mass spectra of each of the derivatized PABA isotopes are shown in FIG. 4. The ratio of M-57+ ion of native compound to known quantities of stable isotope-labeled internal standard was used for quantitation.

Figure 5:
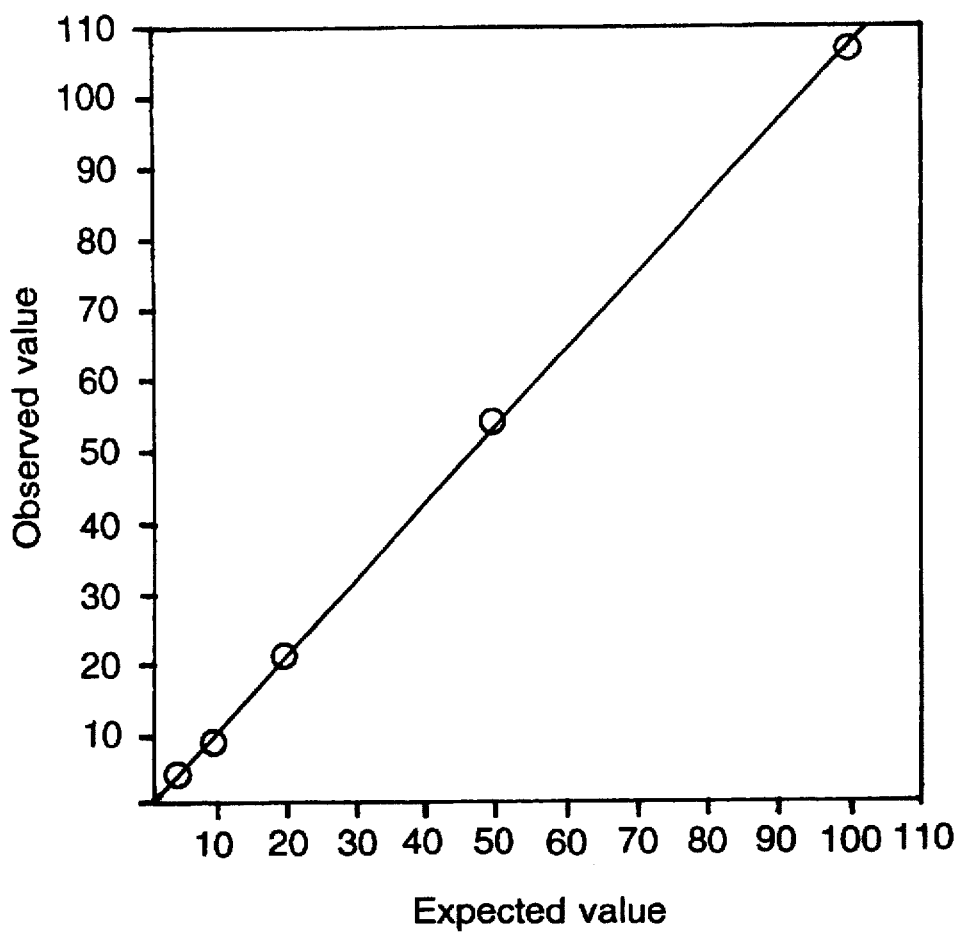
FIG. 5 illustrates calibration curves of MSTBFA derivatized propionyl PABA in water for the ion abundance of varying quantities of PABA to fixed amounts of [$^{13}C_6$] PABA.
Figure 6:
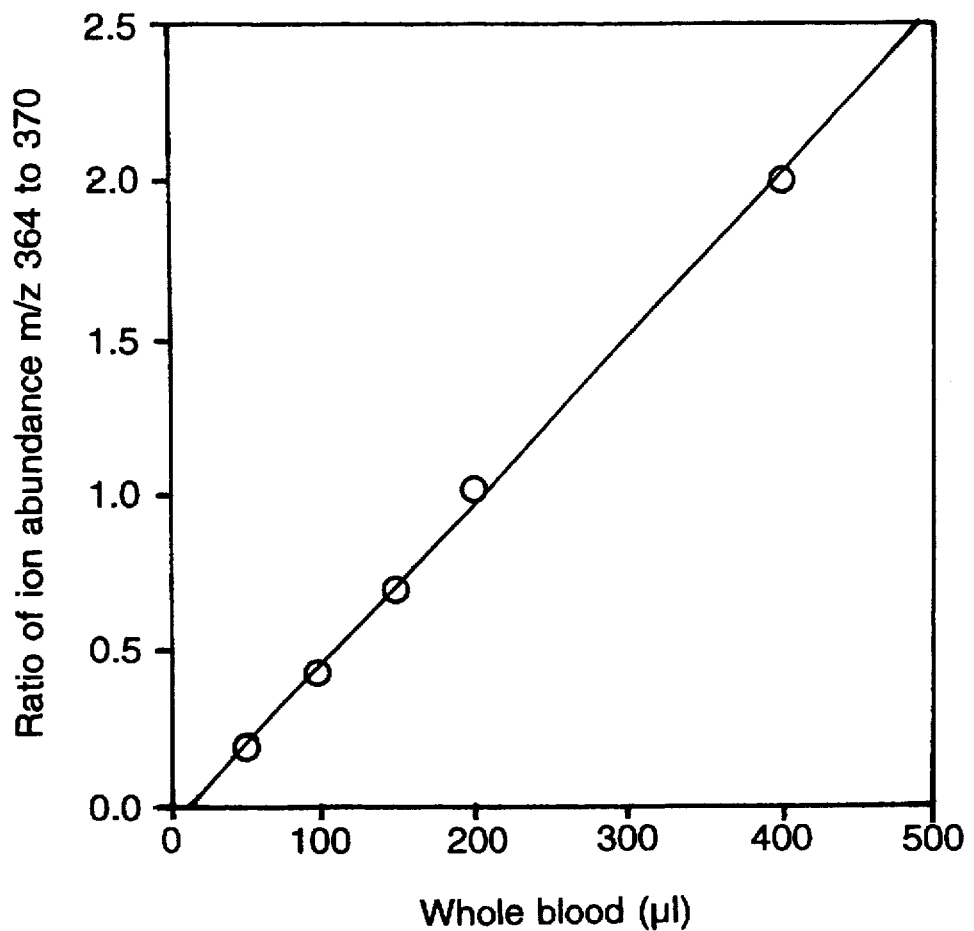
FIG. 6 illustrates calibration curves of MTBSTFA derivatized propionyl PABA derived from a sample in which varying amounts of the same blood sample and fixed amounts of [$^{13}C_6$]PABA incorporating bacterial folate polyglutamate were added.
Figure 7:
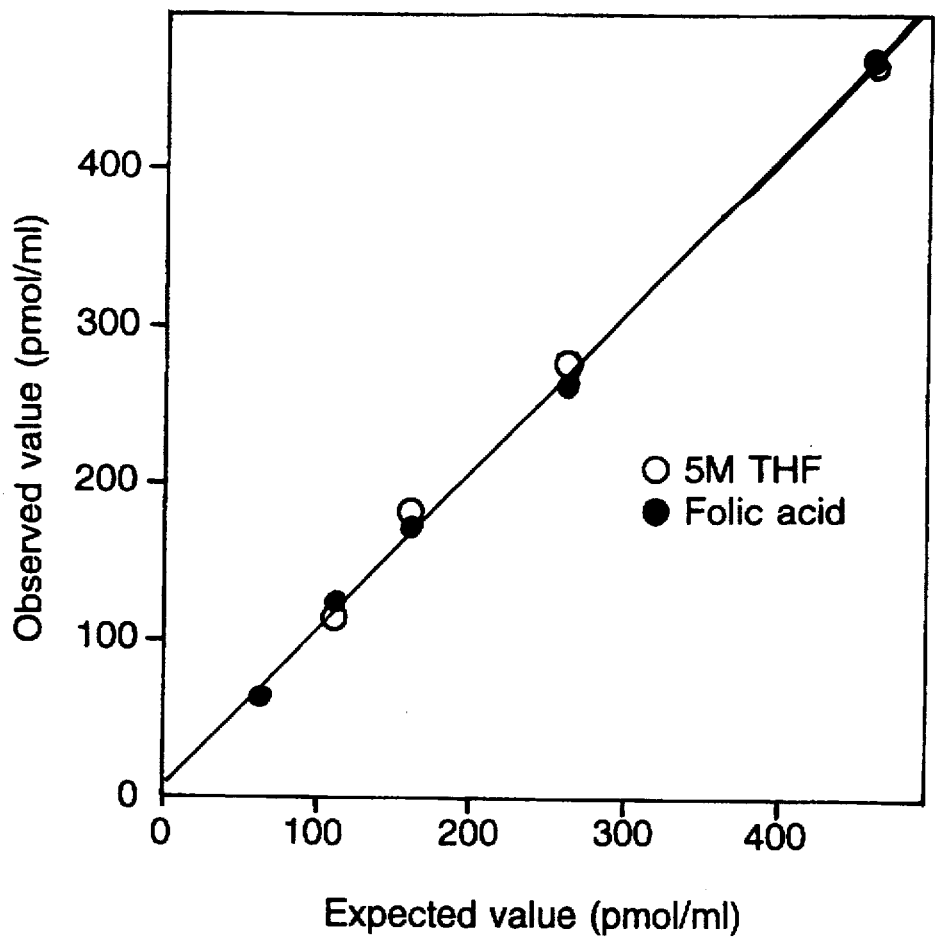
FIG. 7 illustrates calibration curves of total folate content of a blood sample to which varying amounts of 5-methyltetrahydrofolate were added at the outset of sample preparation.

Calibration curves for PABA solution in water are shown in FIG. 5. Calibration curves for increasing amounts of whole blood are shown in FIG. 6. Calibration curves for increasing amounts of 5-methyltetrahydrofolate added to a single blood sample are shown in FIG. 7. The calibration curves were derived by plotting the ratio of the abundance of test compounds to fixed amounts of stable isotope-labeled compounds against increasing quantities of test compounds. For example, varying amounts of 5-methyltetrahydrofolate and a fixed amount of internal standard folates were added to 100 µl of normal whole blood before purification of sample. Each sample was purified and analyzed as described herein. The amount of PABA measured, derived from folate in red blood cells and the added 5-methyltetrahydrofolate, was calculated by multiplying the amount of added internal standard folate at the ratio of abundance at m/z 364 to the abundance at m/z 370. This gave the amount of folate present in 100 µl of whole blood, plus the amount of folate added to the sample at the outset of sample preparation. The measured folate level is plotted against the predicted level based on the addition. The predicted level is the sum of the amount added and the measured value in the normal blood to which no exogenous folate is added. The ratio of the abundances of $^{12}C$-PABA to $^{13}C_6$-PABA when plotted against $^{13}C_6$-PABA was linear at the tested range with a correlation coefficient of 0.997.

Similarly increasing amounts of whole blood from a single sample were added to fixed amounts of bacterial folate polyglutamate internal standard and folates purified as described herein. Folate measured was calculated by multiplying the amount of added bacterial folate polyglutamate internal standard in picomoles with the ratio of abundances at m/z 364 to abundance at m/z 370. This number is the amount of folate present in the quantity of whole blood tested. When the ratio of ions m/z 364 to ions m/z 370 was plotted against the amount of whole blood tested the ratio was linear at the tested range of 50 µl of blood to 400 µl with a correlation coefficient of 0.996.

In the conventional folate assays, eg. radio-isotope assays, microbiological assays, etc., the result is expressed as nanograms of folate per ml of red cells. The way in which this result is expressed is prone to inaccuracy on at least two counts in the result calculation process itself. The numerator of nanograms or micrograms of folate is calculated based on the amount of folate monoglutamate standard used in plotting a standard curve expressed as nanograms or micrograms per ml of red blood cells. This is not a true reflection of the weight of the folate polyglutamate molecule as the weight varies depending on the length of the polyglutamate chain. The denominator, the ml of red cells, is calculated from a hematocrit estimation. The hematocrit itself is not a direct measurement, but a derivation from hemoglobin. Because of this the actual amount of folate (in moles) has not been known until now. The assay described herein measures the amount of folate present in a known amount of blood based on the molar equivalents of folate present in relation to measured hemoglobin and therefore is a true reflection of the amount of folates present in a sample. The calculation of the amount of folate in a given number of red blood cells is possible if the red blood cell count is known. As the calibration curve for whole blood was almost perfectly linear over the tested range of 50 µl to 400 µl (8-fold), the assay is expected to be accurate at a wide range of hemoglobin concentrations. As the variation and abnormality in hemoglobin content in anemias or polycythemias is limited to 3- or 4-fold differences, much wider differences being incompatible with life, the assay is expected to be accurate for a blood sample with any hemoglobin concentration in a physiological setting.

In normal human blood with an average hemoglobin concentration of 14 grams per deciliter, the amount of folate measured falls in the range of about 2.1 to about 14.5 nmoles of folate per gram of hemoglobin.

To determine the lower limits of detection of folates in solution, decreasing quantities of 5-methyltetrahydrofolate were added to fixed amounts of stable isotope-labelled internal standard folates.

The sensitivity of measurement is in the low femtomole range. It is possible to increase sensitivity of measurement several-fold by adjusting sample size and electron multiplier setting in the mass spectrometer as is readily apparent to one of ordinary skill in the art. The use of stable isotope-labeled internal standards and mass spectrometry provides for specificity of the measurement and correction for losses during sample preparation. The stable isotopes used in this method are taught in U.S. Pat. No. 5,306,147 allowed application Ser. No. 08/053,545, incorporated herein by reference.

The method of measurement of red cell folates can be easily adapted for use in other biological samples like cerebrospinal fluid, urine, amniotic fluid etc. or can be used in the measurement of food folates or any other folate-containing mixtures.

The clinical implications of the availability of an accurate measurement of folates and folate coenzyme profiles from a biological sample include the obvious folate deficiency states secondary to malnutrition, maldigestion and malabsorption. With the newly described GC/MS-based folate assay it is possible for the first time to classify folate status based on actual measurement. Deficiency of folates can result from several possible causes including inadequate ingestion, inadequate absorption, inadequate utilization, increased requirement, increased excretion and increased destruction. Alcoholism results in a chronic state of folate depletion due to a combination of causes. The negative folate balance in alcoholism can be further defined by this new method and other hematological abnormalities characterized. Alcoholism is well known to cause macrocytosis which is apparently distinct from the macrocytosis produced by the conventional types of megaloblastic anemia. Hematological abnormalities in alcoholism are probably related to changes in folate coenzyme pools.

Herbert, V. and Zalusky, R., J. Clin. Invest. (1962) 41:1263–1276, and Noronha, J. M. and Silverman, M., In: Vitamin $B_{12}$ and Intrinsic factor (H. C. Heinrich, Ed.) Enke, Stuttgart, independently in 1962 proposed the methyl folate trap hypothesis which contends that 5-methyltetrahydrofolate is not metabolically utilizable in vitamin $B_{12}$ deficiency in humans. The enzyme methionine synthase catalyzes the conversion of homocysteine to methionine using cobalamin as a cofactor converting it to methylcobalamin and 5-methyltetrahydrofolate as a cofactor converting it to tetrahydrofolate. If an abnormality in this conversion occurs as a result of either methionine synthase deficiency or dysfunction or deficiency of availability of cobalamin or methyltetrahydrofolate an accumulation of one or the other substrates is expected to occur. In accordance with the methylfolate trap hypothesis, it is expected that 5-methyltetrahydrofolate will accumulate in tissues and body fluids, including red blood cells, in cobalamin deficiency. The method of measurement of folate coenzymes described herein can measure this accumulation since this invention provides accurate measurements of 5-methyltetrahydrofolate and other folate pools from biological samples. As shown in Scheme III, different forms of folates are required for different metabolic reactions. If an abnormality of one or more of the enzyme systems which need folate coenzymes as cofactors is present, it is expected that the substrates accumulate and can be present inside the cell during the life of the cell or be excreted into extracellular fluids. Therefore, as explained above in relation to the methylfolate trap hypothesis, it is expected that the 5-methyltetrahydrofolate levels will be increased in erythrocytes during the period of $B_{12}$ (cobalamin) deficiency. Similarly differences in the ratios of different coenzyme forms of folate are expected in defects of any of the metabolic pathways shown in FIG. 1.

One of the refinements of the methods of diagnosis of folate deficiency has been the use of assays of homocysteine in serum. U.S. Pat. No. 4,940,658 (Allen et al. issued Jul. 10, 1990) refers to diagnosis of cobalamin and folic acid deficiencies. Both cobalamin and folate are cofactors in Reaction 1 in FIG. 1. A deficiency of either cofactor leads to hematological abnormalities. Deficiency of either cofactor leads to accumulation of homocysteine in serum and urine. In warm-blooded animals, folate deficiency causes elevated homocysteine levels and cobalamin deficiency is diagnosed when homocysteine and methylmalonic acid levels are elevated.

Symptoms of both deficiencies result in serious and potentially life-threatening megaloblastic anemia; however, this premise is based on the assumption that all types of folate deficiency are defects in folate utilization resulting in homocysteinemia (Savage et. al., Am. J. Med. (1994) 96:239–246). Only 76% of folate deficient subjects were shown to have homocysteinemia. As homocysteinemia depends on a specific metabolic block at the methionine synthase reaction, homocysteinemia is expected only in a condition of deficiency of 5-methyltetrahydrofolate in the groups of folate deficiencies. However in an abnormality of any of the other metabolic pathways which require folate coenzymes other than 5-methyltetrahydrofolate, homocysteinemia is not expected. Furthermore, in a conventional folate assay, a subclinical deficiency of folate or a deficiency of a specific coenzyme form could be easily missed, as the conventional assays show only an average level of all folate coenzymes. In the new method described herein, folate coenzyme pools are specifically identifies so that abnormalities associated with specific pathways can be detected.

Shovron et al., British Medical J. (1980) 281:1036–1038, and others have described an association between several neuropsychiatric abnormalities and low or marginal folate levels based on the conventional folate assays. Godfrey et. al., Lancet (1990) 336:393–395, showed that daily folate supplementation with 15 mg daily of 5-methyltetrahydrofolate to patients with major psychiatric disorders resulted in significant clinical and social recovery, particularly in patients with marginal folate levels. The methods described herein for measurement of folate coenzyme pools enables clarification of the defect in the particular folate coenzyme forms in such patients.

A further understanding of this invention can be had from the following non-limiting examples. As used herein, unless especially stated to the contrary, all temperatures and temperature ranges refer to the centigrade system and the terms ambient and room temperature refer to about 20°–25° C. The term percent refers to weight percent and the terms mole and moles refer to gram moles.

EXAMPLES

[$^{13}C_6$]p-aminobenzoic acid (99.1% $^{13}C$), [2,6-$^2H_2$]p-aminobenzoic acid (98.7% D) and [2,3,5,6-$^2H_4$]p-aminobenzoic acid (99.4% D) were custom synthesized by C/D/N Isotopes, Quebec, Canada, according to the methods of U.S. patent application Ser. No. 08/053,545. Folate coenzyme standards were purchased from Dr. B. Schirck's Laboratories, Jona, Switzerland. Stock cultures of *Lactobacillus arabinosum* (ATCC 8014) were obtained from American Type Culture Collection, Rockville, Md. N-methyl-N-t-butyldimethylsilyl trifluoroacetamide (MTBSTFA) was purchased from Regis Chemical Company, Morton Grove, Ill. Anion (AG-MP1) and cation (AG-MP50) exchange resins were purchased from Bio-Rad Laboratories, Richmond, Calif. Kits for measuring hemoglobin and all other chemicals were from Sigma Chemical Company, St. Louis, Mo. or other commercial vendors.

Synthesis of Stable Isotope Labeled Folates by
*Lactobacillus arabinosum*

*Lactobacillus arabinosum* is known to synthesize a mixture of folate coenzymes when PABA is present in the culture medium (Shiota T. (1959) Arch Biochem Biophys 80:155–161). A bacterial cake was brought into 10 ml of semi-defined media as described by Shiota (Shiota T. (1959) Arch Biochem Biophys 80: 155–161), except that the p-aminobenzoic acid (PABA) was substituted with an equal amount of [$^{13}C_6$]p-aminobenzoic acid ([$^{13}C_6$]PABA). The organisms were grown to confluency at 37° C. with loose lids in 20 ml sterile screw-cap tubes over 24 hours. The culture was split 1:100 five times with a final split of 1:100 into 2 L of the medium. After this culture grew to confluency (24 hours), the entire 2 L of culture media was added to 200 L of fresh medium. The culture was maintained at pH 6.8 with 5N NaOH. Aeration was 1 L/min with agitation at 10–15 rpm. After 24 hours the cells were collected with a sharpel and the paste weighing 990 grams was washed by centrifugation at 4° C. in 3 volumes of phosphate-buffered saline at 1500×g for 15 min. The supernatant was decanted and the washing was repeated two more times. The cell pellets were then removed from the containers and stored at −20° C. until further use. The bacterial synthesized mixture of folates was partially purified using 50 grams of frozen bacteria with 200 ml of a solution containing 0.1M ammonium bicarbonate buffer pH 9.6 and 0.3M 2-mercaptoethanol (BME). The suspension of bacteria was heated at 102° C. for 30 min followed by centrifugation at 30,000×g for 30 min. The yellow supernatant was decanted off and 1 ml aliquots were maintained frozen at −20° C. until used. Known quantities of this mixture of bacterial synthesized folates is used as an internal standard (ISF) in measurement of blood or serum containing unknown amounts of folate.

Quantitation of Bacterial Folates Used as an Internal Standard (ISF)

The total [$^{13}C_6$] labeled folate content of the purified bacterial folate mixture was determined on triplicate samples at sample volumes ranging from 25 μl to 100 μL. In another set of triplicate assays, 1 nmol of 5-formyltetrahydrofolate monoglutamate (the quantity determined based upon the extinction coefficient of 31,500 at 287 nm at pH 7 (Temple Jr. C, Elliott RD, Rose JD, Montgomery JA. J. Med. Chem. (1979) 22:731) was added to the same quantities of ISF. The samples for quantitation were then placed in 0.1M ammonium bicarbonate buffer, pH 9.6 with 0.1M BME applied to a column containing 100 mg of strong anion exchange (SAX) resin. After washing with 12 ml of 0.05 ammonium bicarbonate pH 9.6 containing 0.1M BME, the SAX resin with bound folates was incubated at 37° C. for 30 min with 1 ml of a solution consisting of 0.1M BME, 2M NaCl, 0.1M ammonium bicarbonate pH 9.6, and bovine folate binding protein with 3.7 μg of total binding capacity for folic acid (approximately 15 fold excess). Following this incubation, the column effluent was filtered through a 0.20 μm hydrophilic membrane filter (Life Science Products, Denver, Colo.). The samples were then placed in Centricon-30 concentrators (Amicon, Inc., Beverly, Mass.) and subjected to centrifugation at room temperature at 5000×g for 30 min initially and at each subsequent wash and final elution steps. The retentate of these filters was washed with 1 ml of 0.05M ammonium bicarbonate pH 9.6 containing 2N NaCl. After this wash, the retentate was washed with 1 ml of $H_2O$ three times. After changing to a clean filtrate cup, the bound folates in the retentate was eluted with 0.5 ml of 0.2M trifluoroacetic acid two times and which contained 1.0 nmol (based on extinction coefficient of 12,300 at 226 nm in 2M HCl (Doub, L., Vandenbilt, J. M., J. Am. Chem. Soc. (1947) 69:2714) of [2,6-$^2H_2$]p-aminobenzoic acid ([$^2H_2$]PABA). The eluates containing ISF and [$^2H_2$]PABA were mixed and taken to dryness in 2 ml microtubes (Sarstedt, Newton, N.C.) in a vacuum centrifuge. After drying, the samples were resuspended in 200 μl of 6M HCl, were sealed with a screw-cap containing a rubber ring and heated in a 110° C. sand bath for 1 hour. After cooling, 20 μl (10%) was removed and dried in the vacuum centrifuge for subsequent folate assay by RIDA. The remainder of each sample was diluted with 1 ml of $H_2O$. The samples were then passed through a column containing 150 mg of C18 gel (YMC GEL Morris Plains, N.J.). The effluent plus 2 ml of 1M HCl wash was then passed over a column containing 50 mg of AG-MP50 (strong cation exchange resin, SCX). The resin was washed with 12 mls of 0.01 acetic acid in methanol followed by 12 ml of $H_2O$. The samples were eluted into 1.1 ml autosampler vials (Chromatography Research Supplies, Addison, Ill.) with 5M $NH_4OH$ in methanol using three 330 μl volumes. The samples were then dried in a vacuum centrifuge. Samples were treated with 30 μl of propionic anhydride for 15 min and dried again in a vacuum centrifuge. The samples were then derivatized by incubation in 30 μl of a 1:2 mixture (v/v) of MTBSTFA and acetonitrile at 60° C. for 30 min followed by analysis on the GC/MS system as described below.

RIDA was performed as previously described (Antony, A. C. et al., J. Biol. Chem. (1982) 257:10081–10089) for assessment of recovery during various steps in purification. Although this assay employing folic acid monoglutamate in the standard curve does not provide the exact quantitation of the mixture of folate coenzymes in the ISF, it can be used to qualitatively determine overall recovery. For example, in the RIDA actual quantities of 5-formyltetrahydrofolate will be underestimated if folic acid is used in the standard curve and vice versa because of differences in affinity (Stokstad, E. L. R., Physiol. Rev. (1967) 47:83–116). However the relative quantities (or presence or absence) of 5-formyltetrahydrofolate or other folates after various steps in purification can be assessed. This information is sufficient to estimate yields for each step. The relative quantities of folate coenzymes in the starting sample of internal standard was compared to the effluent of the SAX column, the elution of the SAX column, the Centricon-30 filtrate and washes, the Centricon-30 retentate before and after trifluoroacetic acid elution, and 10% of the sample following 6N HCl hydrolysis.

Since some folate coenzymes could be cleaved under the acidic conditions of elution (Eto, I. and Krumdieck, C. L., Anal. Biochem. (1980) 109:167–184; Shane B., Methods Enzymol. (1986) 122:323–330) from the Centricon-30 concentrators, recovery for this phase of the assay was quantified by placing 1 nmol of [$^2H_2$]-PABA in the trifluoroacetic acid elution from the filter.

Preparation of Bovine Folate Binding Protein (BFBP)

Folate binding protein was prepared from dried whey using established methods (Selhub, J. et al., Methods Enzymol. (1980) 66:686–90). Binding ability of BFBP was assessed by the following method: 17.5 μg of folic acid, based on the extinction coefficient of 7200 at 350 nm (Blair, J. A. and Saunders, K. J., Anal Biochem (1970) 34:376), was incubated with 965 μl of a solution of purified BFBP in 0.12M $NaPO_4$ (pH 7.0) and 0.03M NaCl at 37° C. for 30 min. At the end of incubation, the sample as well as control samples containing no BFBP but identical amounts of folic acid and buffer or BFBP only without folic acid were exhaustively dialyzed in 10,000 Mr cut-off dialysis membranes (Spectrapor 10 mm, Spectrum Medical Industries, Los Angeles, Calif.) at 4° C. against a 1000-fold excess of 0.12M NaPO$_4$ (pH 7.0) and 0.03M NaCl. Dialysis fluid was changed four times in 48 hrs. Each sample was then analyzed spectrophotometrically for absorbance at 350 nm. Since the apo BFBP has no absorbance at 350 nm, bound folic acid can be determined by subtracting the absorbance at 350 nm for the folic acid control (with no BFBP) from the absorbance at 350 nm of holo BFBP. The specific activity of the BFBP was 8 μg of folic acid bound per mg of protein. The BFBP solution used for analysis of RBC folates contained 12 μg of folic acid binding ability per ml. The BFBP solution was found to be greater than 99.9% free of folate (i.e., >99.9% apoBFBP) as determined by heat inactivation of BFBP at 98° C. followed by folate assays using previously described RIDA methods (Antony, A. C., et al., J. Biol. Chem. (1982) 257:10081–10089) with folic acid in the standard curve.

GC/MS Analysis

Gas chromatography was performed on a Hewlett-Packard 5890A gas chromatograph using helium as carrier through a 10 m by 0.25 mm (internal diameter) SPB-1 fused silica capillary column (Supelco, Belfont, Pa.). The column head pressure was 50 kPa. The injector port temperature was 250° C. and the initial column temperature was 80° C. A temperature ramp of 30° C./min was applied to a final temperature of 300° C. Ionization was by electron impact at 70 eV. A dwell time of 10 ms was used. Mass spectrometry was performed using a Hewlett Packard 5971A mass detector. The electron multiplier was set at 1500 V for pure standards and 1800 to 2200 V for biological samples. Spectra of standards were determined in the scan mode and quantitation was carried out by selected ion monitoring (SIM). Two μl of derivatized sample was injected onto the capillary column using an automatic falling needle injector (Model 7673A autosampler).

Selected Ion Monitoring (SIM)

Quantitation of PABA was based on the ratio of the $[M-57]^+$ ion (m/z 364 for PABA) to the $[M-57]^+$ ion m/z of known quantities of stable isotope-labeled compounds (m/z 366 for $[^2H_2]$PABA, m/z 370 for $[^{13}C_6]$PABA) using SIM (Deutsch, J. C., Kolhouse, J. F. (1993) Anal. Chem. 65:321–326.34). A SIM computer program was written to analyze PABA, $[^2H_2]$PABA and $[^{13}C_6]$PABA simultaneously following a single injection of 2 μl of derivatized sample.

Calculations

The contributions of the stable isotope-labeled PABA to the monitored ions of native compounds or vice versa were less than 0.5% and no corrections for natural isotopic abundance were applied in calculations of ratios of $[^{13}C_6]$ labeled and natural PABA. In experiments using $[^2H_2]$PABA, correction of 9% natural isotopic abundance of PABA to $[^2H_2]$PABA was used. The following formula was used for quantitation of folate from 100 μl of whole blood to which a known amount of ISF was added at the outset of sample preparation:

Folate (nmols/gm Hb)=((A/B)*C)/D; where A is the isotopic abundance of ion $[M-57]^+$ m/z 364 (PABA), B is the isotopic abundance of ion $[M-57]^+$ m/z 370 ($[^{13}C_6]$PABA), C is the nmol amount of ISF added per 100 μl whole blood and D is the grams of hemoglobin present in 100 μl of whole blood.

Stability of PABA and Stable Isotopes of PABA Under Conditions of Cleavage of Folate Coenzymes It is necessary to ensure that PABA and the stable isotope labels are not destroyed under the conditions of cleavage of folate coenzymes into PABA, pteridines and glutamic acid. In separate experiments, equimolar amounts of PABA and each of the stable isotope-labeled PABAs were incubated in 6M HCl at 110° C. over varying periods of time. At the end of incubation, equimolar amounts of one of the other stable isotope labeled forms of PABA was added and analyzed for PABA content by GC/MS.

Efficiency of Cleavage of Folates to PABA

Efficiency of folate cleavage was assessed by two methods. Equimolar amounts of the eight different authentic folate coenzyme standards and aliquots of ISF were assayed qualitatively by RIDA before and after incubation in 6M HCl. Folate coenzymes cleaved in 6N HCl were dried down and adjusted to pH 7.5 before RIDA. Efficiency of cleavage of these folate coenzyme standards were further assessed quantitatively by GC/MS by including known quantities of $[^2H_2]$PABA before the cleavage procedure.

Human Subjects

All studies involving human subjects were approved by the Human Subjects Committee of the Colorado Multi-Institutional Review Board. Four mls each of blood were drawn to EDTA containing vacutainer tubes from 25 apparently normal individuals, between the ages of 18–60 yrs, after an overnight fast.

Purification and Quantitation of Folate Coenzymes From Whole Blood

100 μl of blood and 0.05 nmol of ISF were added to a 15 ml conical plastic screw cap tube and diluted to a final volume of 5 mls of 0.4% ascorbic acid and 1% Triton X-100. This mixture was heated at 102° C. for 30 min. After the tubes were cooled to room temperature, 70 μl of BME followed by 500 μl of 1M NH$_4$HCO$_3$ buffer pH 9.6 were added and mixed. To this mixture, 100 mg SAX resin was added, mixed and passed through a 3 ml plastic column. The remainder of the purification was as described above for quantitation of ISF except that the C-18 column was not used for purification. Hemoglobin concentrations of the blood samples were measured using the cyanmethemoglobin method as described (Rice, E. W., Clin. Chim. Acta (1967) 18:89).

Effect of Contamination of Blood With PABA, PABAGlu or PABAGlu$_n$

The effect of the presence of PABA, PABAGlu or PABA-Glu$_n$ in a blood sample on RBC folate was tested by the addition of known amounts of PABA, PABAGlu or PABA-Glu$_5$ to aliquots of a blood sample and subsequent folate assay by GC/MS. Similarly the effect of acute or chronic PABA ingestion on RBC folate levels was tested by analysis of blood from two subjects, one of whom ingested PABA on a chronic basis.

GC/MS Characterization of PABA

The ratio of $[M-57]^+$ ions of derivatized PABA (m/z 364) to that of derivatized $[^{13}C_6]$PABA (m/z 370) was used for quantitation. An example of the structure of the $[M-57]^+$ ion generated from MTBSTFA-derivatized propionated p-aminobenzoic acid is shown below:

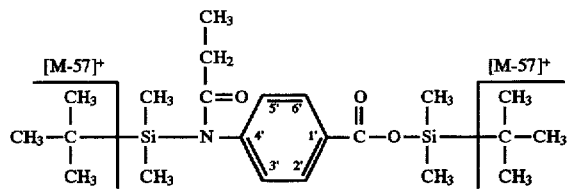

The total ion chromatograms of PABA, [$^2$H$_2$]PABA and [$^{13}$C$_6$]PABA purified from the internal standard are shown in FIG. 1. The mass spectra of PABA, [$^2$H$_2$]PABA and [$^{13}$C$_6$] PABA are shown in FIG. 3. The M$^+$, the total mass of derivatized products and putative structure of fragments of each compound is shown in Table 1. The differences in mass between PABA, [$^2$H$_2$]PABA and [$^{13}$C$_6$]PABA is shown in each of the ion fragments as differences of 2 and 6 daltons respectively. Calibration curves of increasing amounts of PABA to fixed amounts of [$^{13}$C$_6$]PABA in aqueous solution showed a correlation coefficient (r) of 0.999. Calibration curves were derived by plotting the ratio of the abundances of m/z 364 (PABA) to m/z 370 ([$^{13}$C$_6$]PABA), representing measured PABA against increasing quantities of added PABA. A similar calibration curve plotted for increasing quantities of whole blood against fixed quantities of ISF is shown in FIG. 5. The ratio of measured folates to increasing amounts of whole blood was linear at the tested range with a correlation coefficient (r) of 0.997. Similar calibration curves plotted for increasing quantities of folic acid or 5-methyltetrahydrofolate, added to fixed amounts of a blood sample, against fixed quantities of ISF are shown in FIG. 6. The ratio of measured folates to increasing amounts of whole blood was linear at the tested range with a correlation coefficient (r) of 0.998.

Quantitation of Three Pools of Folates

Pool I consists of tetrahydrofolate, dihydrofolate, 5,10-methylene tetrahydrofolate, and 5-methyldihydrofolate.

Pool II consists of 5-methyltetrahydrofolate.

Pool III consists of 5-formyltetrahydrofolate, 10-formyltetrahydrofolate, 5-formiminotetrahydrofolate, 5,10-methenyltetrahydrofolate, and folic acid.

Method

The purified folates are eluted with 0.1N HCl, in place of trifluoro-acetic acid, from Centricon-30 filters (containing folates purified from red blood cells and from the internal standard mixture) and are split into three equal portions (A, B and C) and incubated at 37° C. for two hours. They are further processed as follows:

Sample A and Sample C are vacuum-dried at the end of two hours.

At the end of 2 hours, the pH of Sample B is raised to approximately 12 by adding 1N NaOH and the sample is incubated at room temperature for four hours or 16–24 hours at 4° C., and then the sample is brought to a final pH of 1 with HCl, incubated for one hour at room temperature and then vacuum-dried.

The dried samples A and B are brought into solution (final volume 1 ml) at pH 9.6 in a mixture of 400 µl 5M NaCl, 100 µl 1M NH$_4$HCO$_3$ buffer pH 9.6, 100 µl BFBP and 400 µl water, mixed and incubated at 37° C. for 30 min. This incubation is performed to bind all uncleaved folates to BFBP. At the end of incubation, the samples are placed in Centricon-30 filters and filtered to remove PABA and PABAGlu$^n$ as described above with respect to measurement of total folates. The uncleaved folates bound to BFBP are eluted in 0.1N HCl as described above with respect to measurement of total folates. The eluates are vacuum-dried.

To dried samples A, B and C are added 0.5 nmol of [$^2$H$_2$]-paraaminobenzoic acid as a second internal standard and the mixture is incubated in 200 µl 6N HCl at 110° C. for 60 min. The samples are further processed and analyzed on the GC/MS as described above with respect to measurement of total red blood cell folates. The following formulas are used to find proportions of different pools.

Total folate=(x/y)*z where x=ion abundance of m/z 364 y=ion abundance of m/z 370 z=amount of [$^{13}$C$_6$]-labeled internal standard folate mixture added at the outset of sample purification.

Ratios of ion abundances of m/z 364 relative to m/z 366 are determined on Samples A, B and C.

This ratio is chosen because m/z 366 is derived from [$^2$H$_2$] paraaminobenzoic acid (added after differential cleavage processes).

Pool I%=((C−A)/C)*100

Pool II%=((A−B)/C)*100

Pool III%=(B/C)*100 where A is ratio of abundance of ion m/z 364 to 366 of Sample A (folates remaining after removal of Pool I folates, i.e., represents Pools II+III); B is ratio of abundance of ion m/z 364 to 366 of Sample B (folates remaining after removal of Pools I+II folates, i.e., represents Pool III); C is ratio of abundance of ion m/z 364 to 366 of Sample C (represents total folates in the sample).

An example of application of this method to folates present in chicken liver is provided in Table 2.

An example of application of this method to folates present in red blood cells of two normal individuals is shown in Table 3.

TABLE 2

Folates* in Chicken Liver

| | 364 | 366 | 370 | Total folates in nmol/gm | 364/366 | 370/366 | Pool I % | Pool II % | Pool III % |
|---|---|---|---|---|---|---|---|---|---|
| 2a 500 mg chicken liver + 0.575 nmol ISF | 321.3 | 15.59 | 3.61 | | 20.61 | 0.23 | | | |
| 2b | 103 | 10.92 | 1.14 | | 9.43 | 0.10 | | | |
| 2c | 623.7 | 27.07 | 6.87 | 104 | 23.04 | 0.25 | 10.55 | 48.51 | 40.94 |

*total folates = ratio of ion 364 to 370 × amount of ISF (stable isotope-labeled internal standard folate) × 2

TABLE 3

Red blood cell folates on two normal individuals

| Patient* | | 364 | 366 | 370 | total folate nmol/ml | 364/366 | Pool I | Pool II | Pool III |
|---|---|---|---|---|---|---|---|---|---|
| 1a** | 600 μl SK rbc + 10 μl IS | 2064 | 8243 | 698 | | 0.25 | 72.73 | 1.258 | 28.53 |
| 1b | | 1957 | 7471 | 587 | | 0.26 | | | |
| 1c | | 6717 | 7316 | 1126 | 1.15 | 0.92 | | | |
| 2a | 600 μl KH rbc + 10 μl IS | 1614 | 3321 | 338 | | 0.49 | 41.09 | 27.69 | 31.22 |
| 2b | | 2143 | 8320 | 629 | | 0.26 | | | |
| 2c | | 4886 | 5923 | 842 | 1.112 | 0.82 | | | |

*Patient 2 is on folate supplements, 2 mg/day for the past 3 months.
**a = Pools II + III, b = Pool III, c = total Pool I = c – ac * 100, Pool II = a – b/c * 100, Pool III = b/c * 100

Stability of PABA Isotopes Under Conditions of Folate Cleavage

The stable isotope labels at the 2 and 6 positions of [2,6-$^2$H$_2$]p-aminobenzoic acid were not exchanged with hydrogen during acid incubation for up to 120 hrs at 110° C. However, the stable isotope labels at the 3 and 5 positions of [2,3,5,6-$^2$H$_4$]p-aminobenzoic acid were found to exchange for hydrogen under the conditions of folate cleavage. Incubation in 6N HCl at 110° C. for one hour resulted in exchange of greater than 10% of deuterium labels at the 3 and 5 positions for hydrogen. The exchange was complete at 24 hours.

Yield of Folates During Purification and Completeness of Cleavage to PABA

RIDA's performed on RBC samples during various stages of sample preparation showed an overall recovery of greater than 95% folates relative to the starting material. Qualitative RIDA and quantitative GC/MS analysis to assess efficiency of cleavage of individual folate coenzymes and ISF showed that all folate coenzymes were completely cleaved into PABA during incubation in 6N HCl at 110° C. for 60 min.

Quantitation of Bacterial Folates (ISF)

Calibration curves were generated by adding fixed amounts of [$^2$H$_2$]PABA to varying amounts of ISF before cleavage to PABA. The ratio of abundances of m/z 370 ([$^{13}$C$_6$]PABA) to m/z 366 ([$^2$H$_2$]PABA) were plotted against the amount of ISF added. Since the quantity of folates relate to PABA on an equimolar basis, the molar equivalents of folates were calculated from the ratios. Calculations were also made from similar samples where known quantities of 5-formyltetrahydrofolate were added to ISF before purification. Based on these values, the concentration of internal standard folates in solution was determined to be 11.55 nmols/ml. The ISF were more than 99.5% enriched with [$^{13}$C$_6$]labeled folates.

Stability of ISF

Partially purified ISF were stored in 0.3M BME at –20° C. in solution in aliquots of 500 μl. The effect of multiple freezing and thawing of the same lot of folates was tested using [$^2$H$_2$]PABA as the standard. The ISF were found to withstand the effects of multiple freezing and thawing with loss of activity of <5% for 16 freeze-thaw cycles over more than an year. The ISF showed <1% breakdown when stored at –20° C. for a period of greater than two years.

Precision

Intra-assay precision was determined by purification and analysis of five aliquots of a single blood sample. The coefficient of variation of measurement was 4.7%. The inter-assay precision was determined by measuring folates from different aliquots of a single blood sample stored at –20° C., ten times over a period of 6 months and was found to be 4.5%.

Sensitivity

To determine the lower limits for detection of PABA in aqueous solution, decreasing quantities of PABA were added to fixed amounts of stable isotope labelled PABA and assayed with an EM setting of 3000 V in the SIM mode. The limit of detection of PABA was 2 fmol with a signal to noise ratio of 2. Aliquots of a single blood sample, in different dilutions, to each of which a known quantity of internal standard was added, were processed and the lower limit of quantitation was determined to be less than 500 fmol of folate per ml of whole blood (3.4 pmol/gm Hb).

Effect of Extraneous or Ingested PABA on Folate Levels

The effect of contamination of a blood sample with a 120 fold molar excess (compared to endogenous folate) of PABA, PABAGlu or PABAGlu$_5$ is shown in Table 4. The effect of acute ingestion of PABA on RBC folates is shown in Table 5. Analysis of RBC folate from the blood of a single subject, who was ingesting tablets of 850 mg PABA daily for more than a year and had stopped the tablets one week before folate assay, showed a measured folate level of 3.1 nmol per gm of Hb and a serum PABA of 0.2 nmol/ml. There was no artifactual increase in measured folates due to potential PABA accumulation in RBCs. The baseline RBC folate in this individual was not known.

TABLE 4

Lack of effect of addition of a 120-fold molar excess (relative to folate) of PABA, PABAGlu or PABAGlu$_n$, to blood samples on RBC folate levels

| | Measured folate (nmol/gm Hb) |
|---|---|
| 200 μl blood, no addition | 5.8 |
| 200 μl blood + 10 nmol PABA | 5.8 |
| 200 μl blood + 10 nmol PABAGlu | 5.7 |
| 200 μl blood + 10 nmol PABAGlu$_5$ | 5.7 |

TABLE 5

Lack of effect of acute PABA ingestion on RBC folates

| | Measured folate (nmol/gm Hb) | Serum PABA (nmol/ml) |
|---|---|---|
| Fasting blood sample | 6.5 | 0.03 |
| 4 h blood sample after 850 mg PABA | 6.1 | 30.32 |
| 24 h blood sample after two 850 mg doses of PABA (second dose at 18 hours | 5.8 | 33.71 |

Reference Range

The reference range of RBC folate values of 25 normal individuals showed a range of folate values from 2.1 to 14.5 nmol/gm Hb (mean 7.2, SD 3.6).

Cobalamin Deficiency

If the methylfolate trap hypothesis is true, this method can be used to diagnose cobalamin deficiency since 5-methyltetrahydro-folate (Pool II in our system) will be disproportionately increased in tissues including red blood cells.

In order to confirm the association between neuropsychiatric disorders and deviations from normal folate profiles, blood samples from 25 normal individuals and from 50 randomly chosen psychiatric inpatients were analyzed for total folates and folate coenzymes. Of the 50 psychiatric inpatients, no patients were found to have low serum folate and none were found to have low RBC folates based on the conventional competitive binding assay. However, four patients were found to have low red cell folates (more than two standard deviations below the mean normal range).

While various embodiments of the present invention have been described in detail, it is apparent that the modifications and adaptations will occur to those skilled in the art. However, it is to be expressly understood that such modifications and adaptations are within the spirit and scope of the present invention, as set forth in the following claims.

We claim:

1. A method for determination of concentration in a body fluid of at least one member of an endogenous folate co-enzyme pool selected from the group consisting of:

(1) pool I consisting essentially of tetrahydrofolate, dihydrofolate and 5,10-methylenetetrahydrofolate;

(2) pool II consisting essentially of 5-methyltetrahydrofolate; and (3) pool III consisting essentially of 3-formyltetrahydrofolate, 10-formyltetrahydrofolate, 5,10-methyleneyltetrahydrofolate, and 5-formiminotetrahydrofolate, said method comprising the steps of:

(a) combining a known amount of at least one internal standard folate co-enzyme which is a non-radioactively-labeled stable isotope of a member of the selected folate co-enzyme pool with said body fluid, wherein said internal standard folate coenzyme is recovered from harvested bacterial cells grown on a medium containing non-radioactively-labeled stable isotope paraaminobenzoic acid;

(b) at least partially purifying the endogenous and internal standard folate coenzymes from other components in said body fluid in a partial purification step;

(c) quantitating the endogenous folate co-enzymes in the purified body fluid of step (b) by gas chromatography/mass spectrometry analysis; and (d) determining the concentration of the selected endogenous folate coenzyme pool by correcting the concentrations of endogenous folate coenzymes quantitated in step (c) for endogenous losses as reflected by losses in the known amount of internal standard folate co-enzyme of step (a).

2. The method of claim 1 wherein said internal standard is prepared by a method comprising adding $^{13}C_6$-labeled paraaminobenzoic acid to a growth medium for *Lactobacillus arabinosus*, harvesting cells thereof grown on said growth medium to collect harvested cells, and recovering said internal standard from said harvested cells.

3. The method of claim 1 wherein the body fluid is selected from the group consisting of whole blood, serum, plasma, cerebrospinal fluid and amniotic fluid.

4. The method of claim 1 wherein the partial purification step (b) comprises the steps of:

(a) binding said folates to a strong anion exchange resin to form bound folates;

(b) exchanging the bound folates of step (a) from the anion exchange resin by binding them to folate binding protein to form protein-bound folates; and (c) filtering the protein-bound folates of step (b) to remove contaminating paraaminobenzoic acid and PABA Glu.

5. The method of claim 1 also comprising the step of derivatizing the endogenous and internal standard folates in said purified body fluid of step (b) prior to step (c).

6. The method of claim 5 wherein the derivatization step is performed by reacting the endogenous and internal standard folates in said purified body fluid with N-methyl-t-butyldimethylsilyltrifluoroacetamide.

* * * * *